US008491528B2

(12) United States Patent
Muri et al.

(10) Patent No.: US 8,491,528 B2
(45) Date of Patent: Jul. 23, 2013

(54) CRITICAL ALIGNMENT OF FLUIDICS CASSETTES

(75) Inventors: John I. Muri, Aliso Viejo, CA (US); Craig Edwards, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1247 days.

(21) Appl. No.: 11/558,403

(22) Filed: Nov. 9, 2006

(65) Prior Publication Data
US 2008/0114311 A1 May 15, 2008

(51) Int. Cl.
*A61M 37/00* (2006.01)
(52) U.S. Cl.
USPC ............ 604/131; 604/27; 604/294; 604/295; 604/298; 600/401; 417/477.2
(58) Field of Classification Search
USPC ........... 604/131, 294–295, 298, 27; 600/401; 417/477.2
See application file for complete search history.

(56) References Cited

U.S. PATENT DOCUMENTS

| 4,193,004 A | | 3/1980 | Lobdell et al. | |
| 4,537,561 A | * | 8/1985 | Xanthopoulos | 417/63 |
| 4,758,220 A | | 7/1988 | Sundblom et al. | |
| 4,773,897 A | | 9/1988 | Scheller et al. | |
| 4,920,336 A | | 4/1990 | Meijer | |
| 5,006,110 A | | 4/1991 | Garrison et al. | |
| 5,020,535 A | * | 6/1991 | Parker et al. | 606/174 |
| 5,091,656 A | * | 2/1992 | Gahn | 307/119 |
| 5,125,891 A | | 6/1992 | Hossain et al. | |
| 5,195,960 A | | 3/1993 | Hossain et al. | |
| 5,230,614 A | | 7/1993 | Zanger et al. | |
| 5,282,787 A | | 2/1994 | Wortrich | |
| 5,454,783 A | | 10/1995 | Grieshaber et al. | |
| 5,470,312 A | * | 11/1995 | Zanger et al. | 604/34 |
| 5,499,969 A | * | 3/1996 | Beuchat et al. | 604/30 |
| 5,676,530 A | | 10/1997 | Nazarifar | |
| 5,697,910 A | * | 12/1997 | Cole et al. | 604/153 |
| 5,747,824 A | | 5/1998 | Jung et al. | |
| 5,871,492 A | * | 2/1999 | Sorensen | 606/166 |
| 5,899,674 A | | 5/1999 | Jung et al. | |
| 5,928,257 A | * | 7/1999 | Kablik et al. | 606/180 |
| 6,024,428 A | | 2/2000 | Uchikata | |
| 6,117,126 A | | 9/2000 | Applebaum et al. | |
| 6,511,454 B1 | | 1/2003 | Nakao et al. | |
| 6,632,214 B2 | | 10/2003 | Morgan et al. | |
| 6,962,488 B2 | | 11/2005 | Davis et al. | |

(Continued)

FOREIGN PATENT DOCUMENTS

EP 1310267 5/2003
EP 1787606 A1 5/2007

(Continued)

*Primary Examiner* — Kevin C Sirmons
*Assistant Examiner* — Edelmira Bosques
(74) *Attorney, Agent, or Firm* — Abbott Medical Optics Inc.

(57) ABSTRACT

Devices, systems, and methods interface a cassette with an eye treatment system console to provide coupling between the console and an eye treatment probe. The console may receive the cassette using a driven axial translation linkage that inhibits rotation of the cassette. The cassette may facilitate accurately positioning of a pressure sensor relative to a the console by allowing sliding movement between the sensor and a cassette body. Multiple peristaltic drives may be mounted to the console so that their rotors rotate about a common axis. An integrated mount structure may support and/or position components of the console which will interface with cassette, and an axially compressible vacuum connector of the console seal to a tapered vacuum coupler of the cassette.

13 Claims, 18 Drawing Sheets

U.S. PATENT DOCUMENTS

| | | |
|---|---|---|
| 7,070,578 B2 | 7/2006 | Leukanech et al. |
| 7,244,240 B2 | 7/2007 | Nazarifar et al. |
| 2001/0051788 A1 | 12/2001 | Paukovits et al. |
| 2003/0108429 A1 | 6/2003 | Angelini et al. |
| 2005/0069419 A1 | 3/2005 | Cull et al. |
| 2005/0070859 A1 | 3/2005 | Cull et al. |
| 2005/0095153 A1* | 5/2005 | Demers et al. ............ 417/477.2 |
| 2005/0245888 A1 | 11/2005 | Cull |
| 2007/0049898 A1 | 3/2007 | Hopkins et al. |
| 2008/0066542 A1 | 3/2008 | Gao |
| 2008/0114289 A1 | 5/2008 | Muri et al. |
| 2008/0114311 A1 | 5/2008 | Muri et al. |

FOREIGN PATENT DOCUMENTS

| | | |
|---|---|---|
| EP | 1873501 A1 | 1/2008 |
| EP | 1867349 | 11/2008 |
| WO | 93/24082 | 12/1993 |
| WO | 98/18507 | 5/1998 |
| WO | WO 99/17818 | 4/1999 |
| WO | WO 02/34314 A1 | 5/2002 |
| WO | 2005/084728 | 9/2005 |
| WO | WO 93/17729 | 11/2006 |
| WO | WO 2007/143677 A2 | 12/2007 |

* cited by examiner

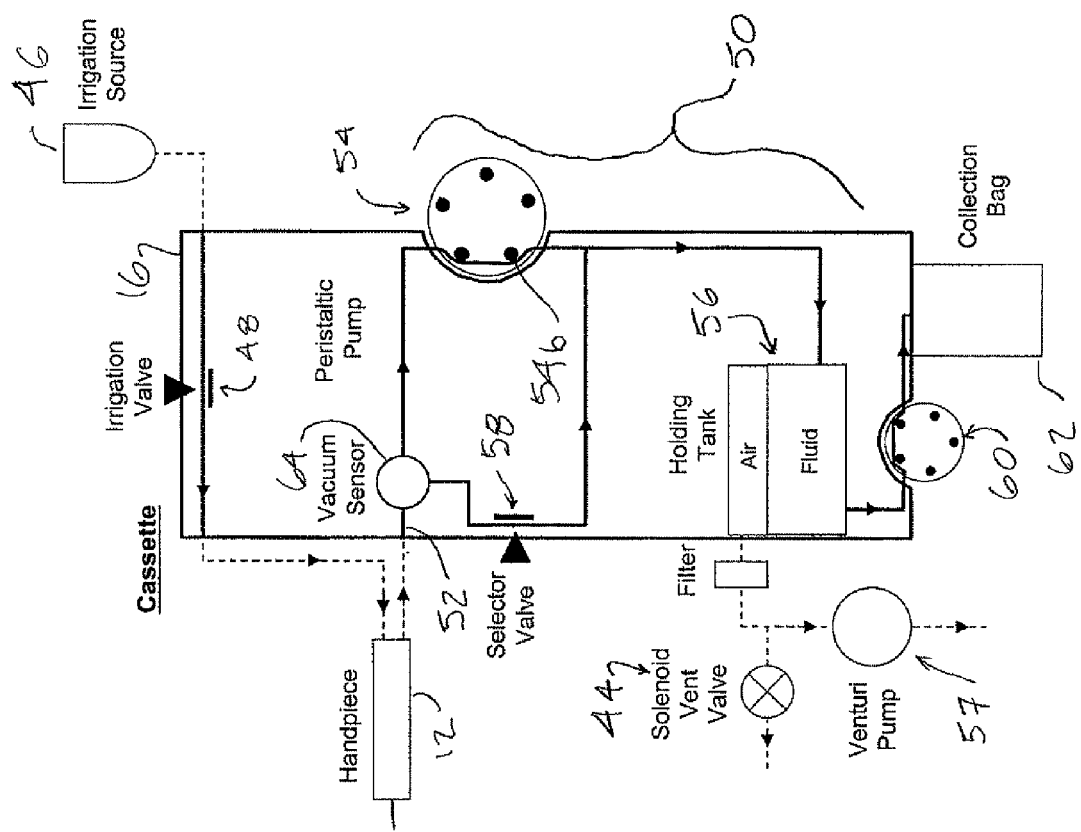

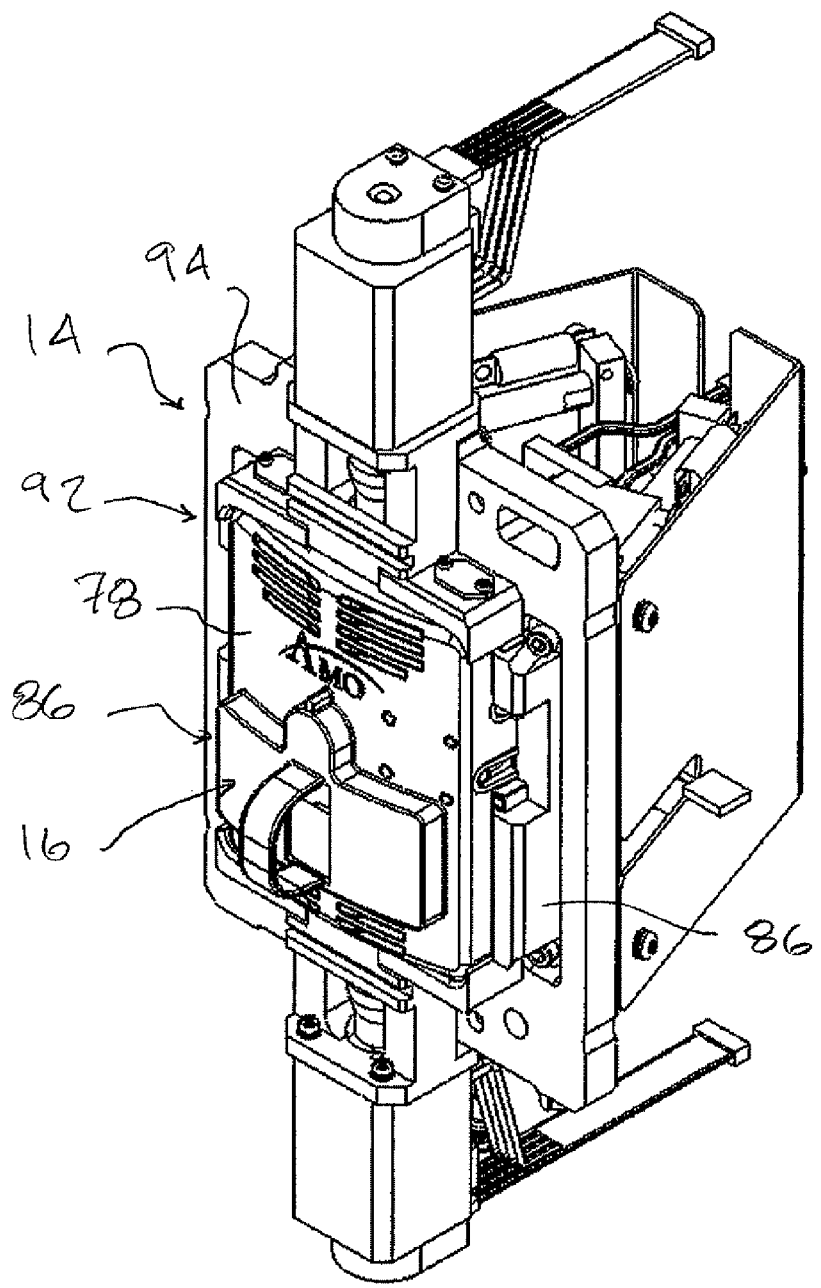
FIG_3A

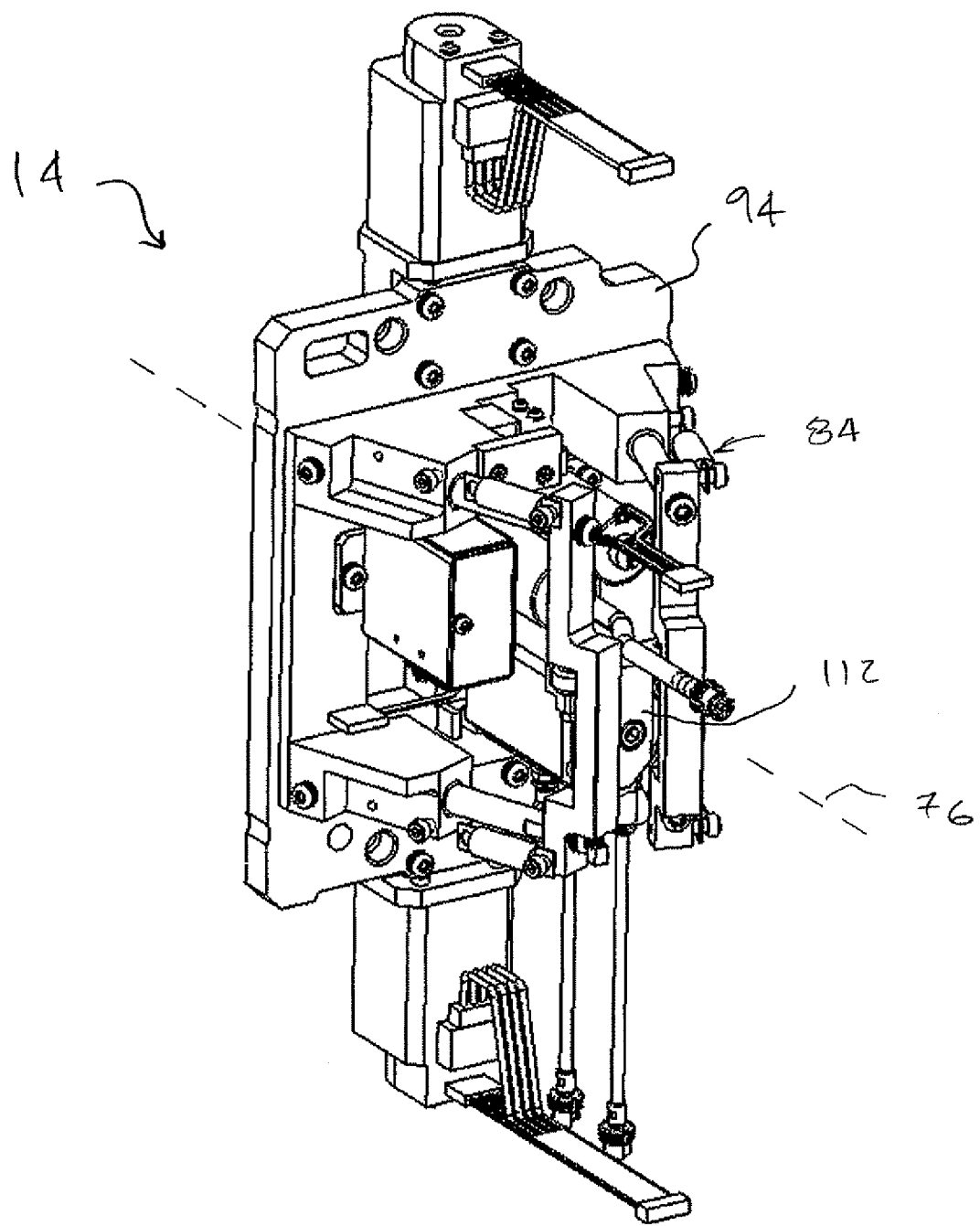
FIG_4

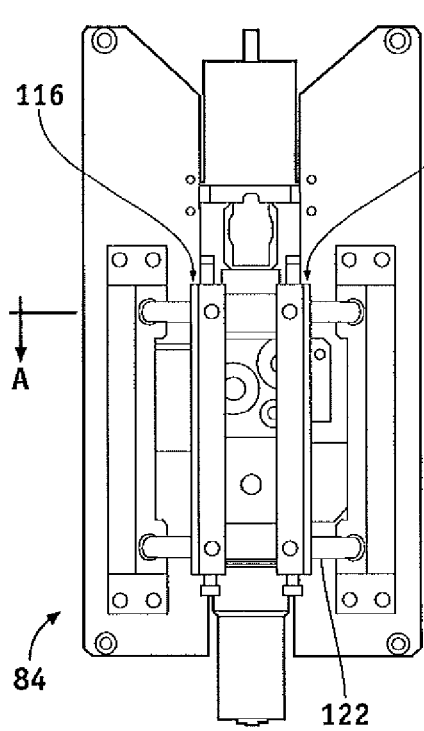
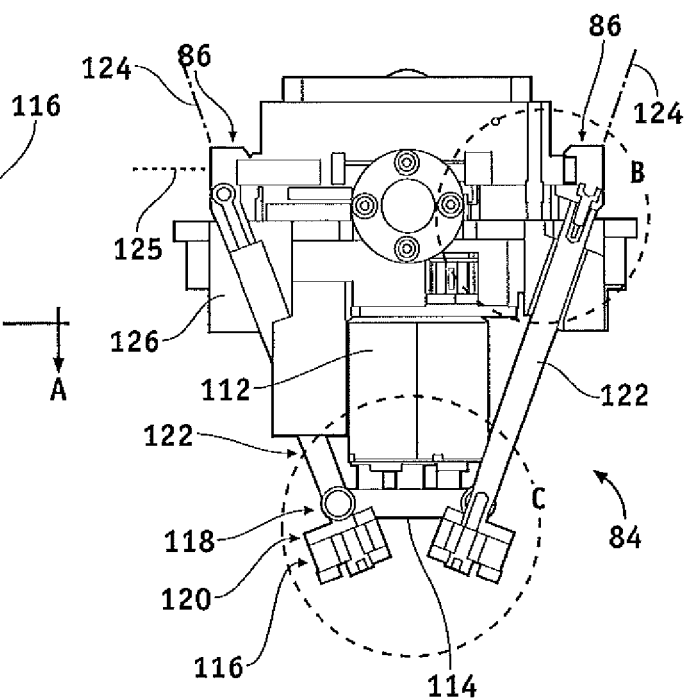
FIG. 4A
FIG. 4B
SECTION A-A
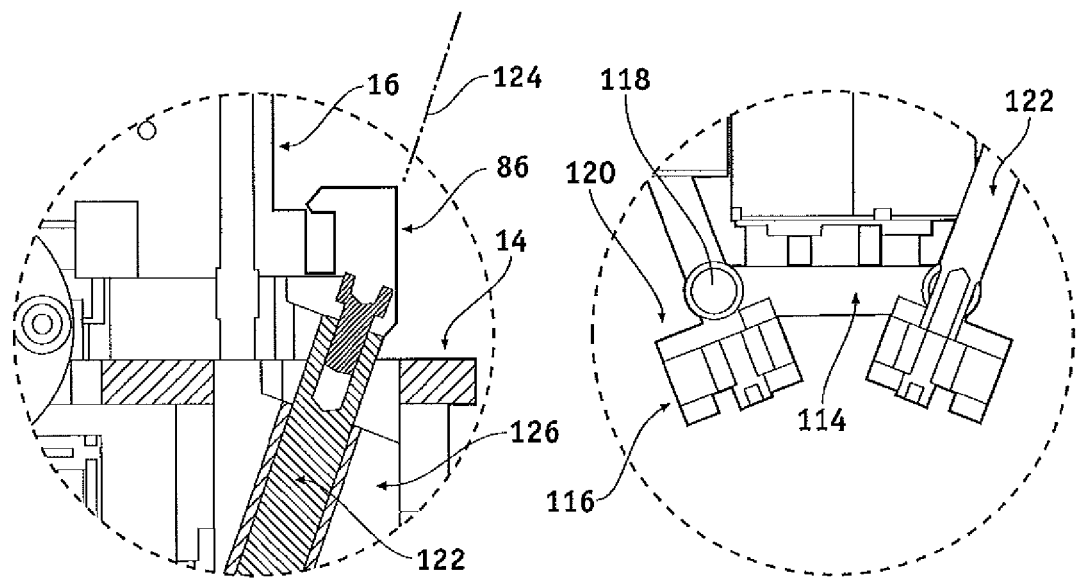
FIG. 4C
DETAIL B
FIG. 4D
DETAIL C

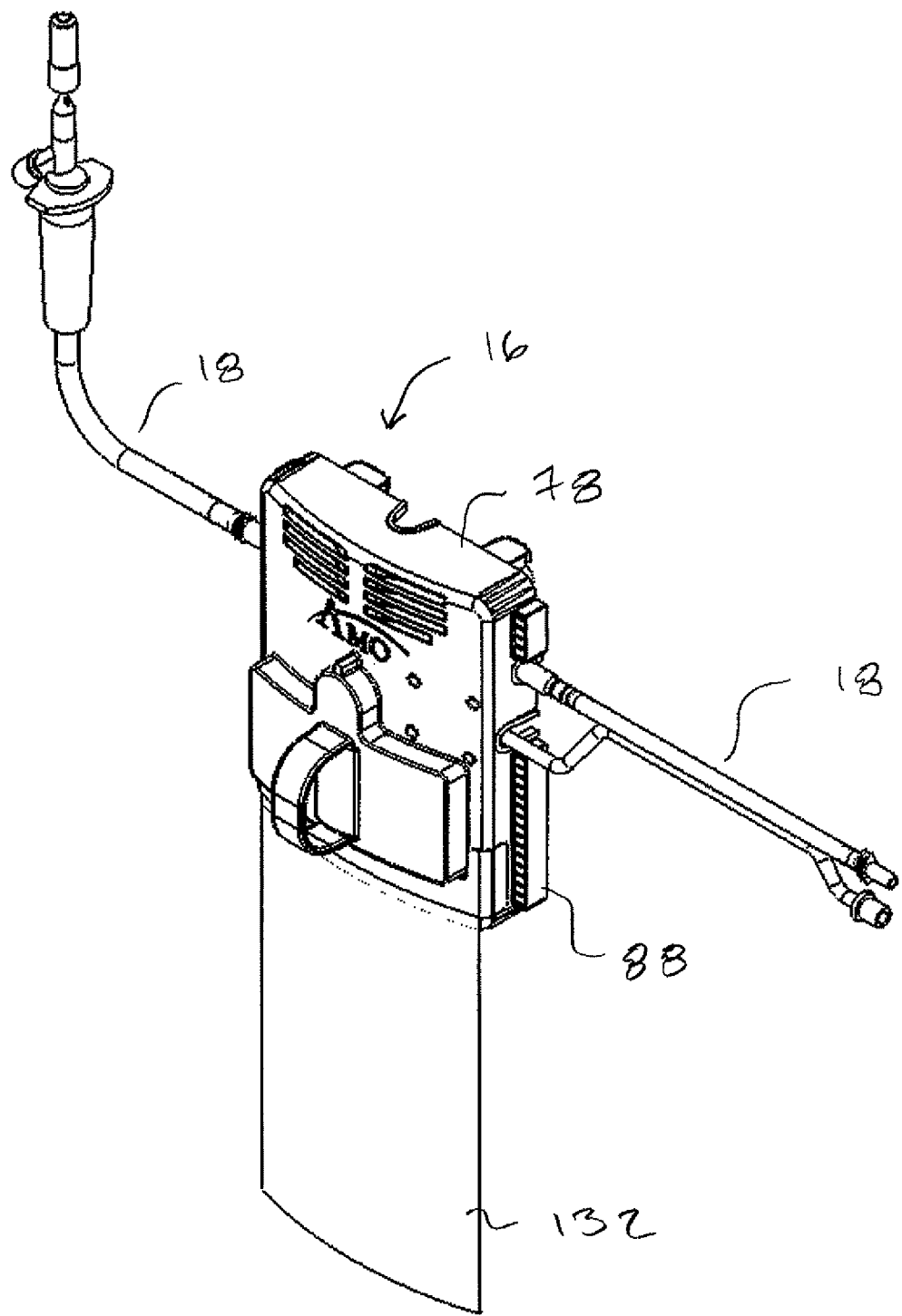
FIG_5

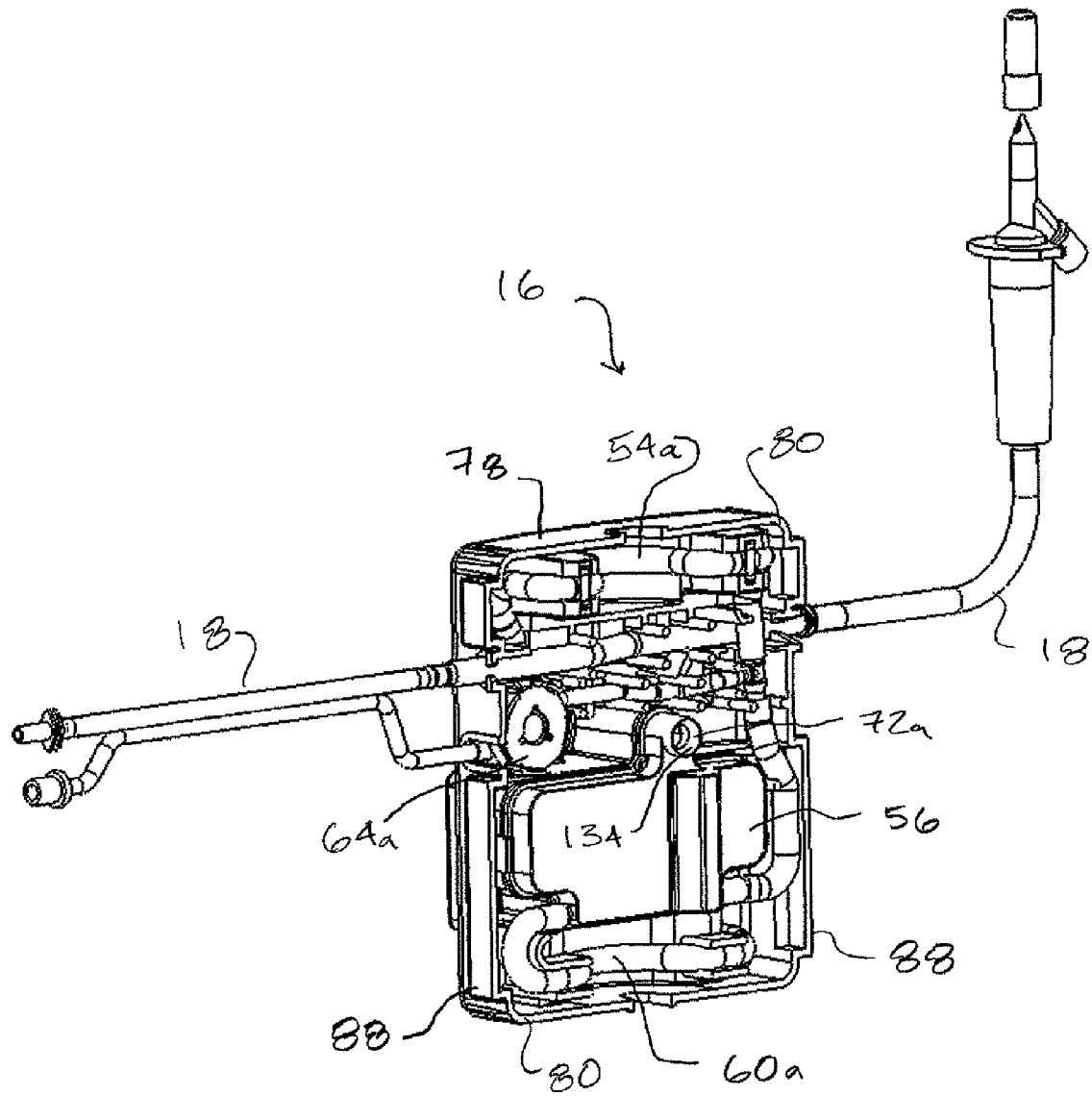
FIG_5A

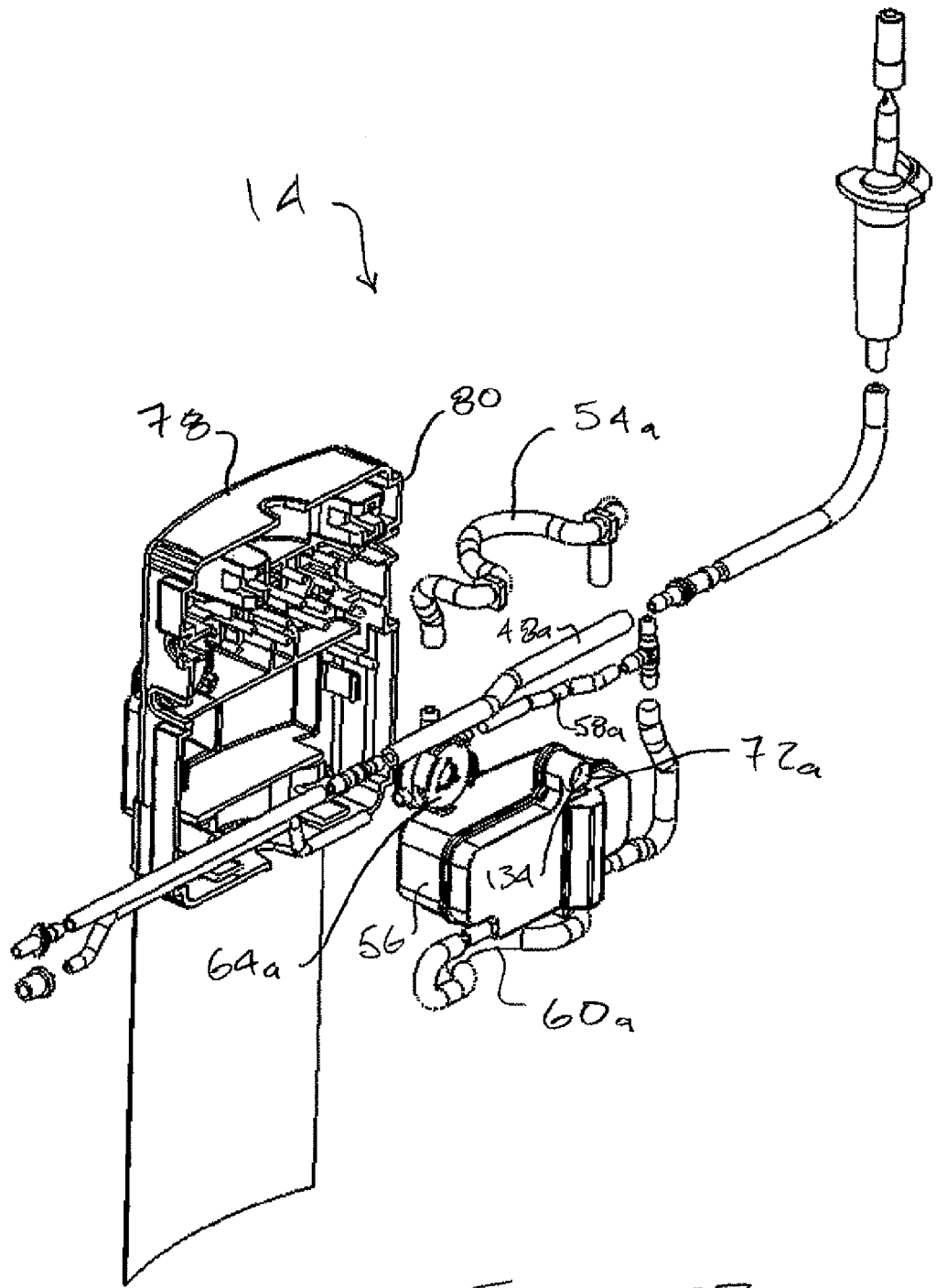
FIG_5B

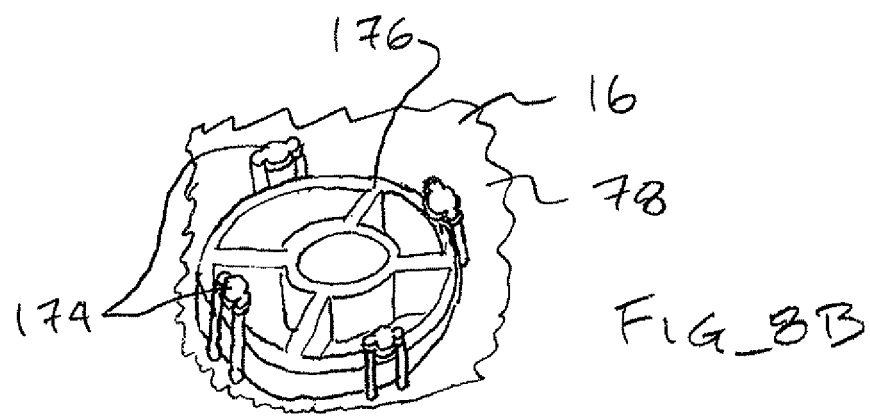
FIG_8B
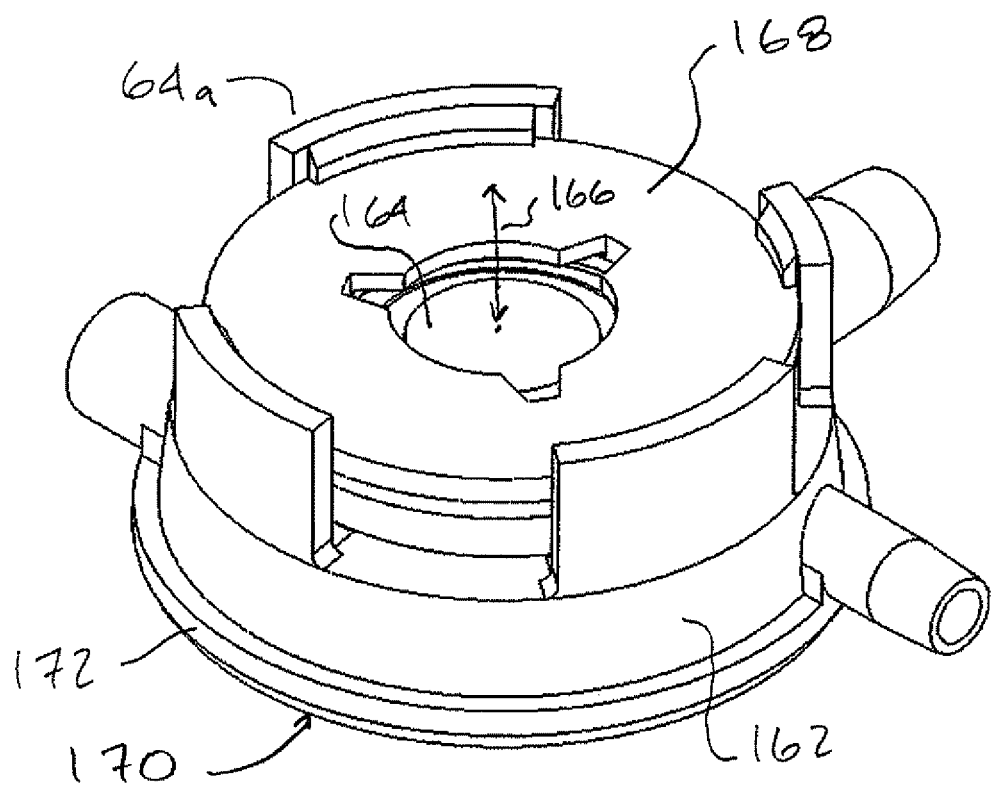
FIG_8

CRITICAL ALIGNMENT OF FLUIDICS CASSETTES

BACKGROUND OF THE INVENTION

The present invention is generally related to methods, devices, and systems for controlling surgical fluid flows, often during treatment of an eye. In exemplary embodiments, the invention facilitates mounting of a cassette onto a surgical console so as to couple the console to a treatment probe, with the cassettes optionally comprising disposable structures having conduit networks for providing both irrigation and aspiration during treatments of anterior and/or posterior chambers of the eye, including phaeoemulsification of cataracts, treatment of retinal diseases, and the like.

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil and within a capsular bag, the capsular bag being a thin, relatively delicate structure which separates the eye into anterior and posterior chambers.

With age, clouding of the lens or cataracts are fairly common. Cataracts may form in the hard central nucleus of the lens, in the softer peripheral cortical portion of the lens, or at the back of the lens near the capsular bag. Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humor in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, aspiration flow systems can generally be classified in two categories: 1) volumetric-based aspiration flow systems using positive displacement pumps; and 2) vacuum-based aspiration systems using a vacuum source, typically applied to the aspiration flow through an air-liquid interface within a holding tank Among positive displacement aspiration systems, peristaltic pumps (which use rotating rollers that press against a flexible tubing to induce flow) are commonly employed. Cassette systems can be used to couple peristaltic pump drive rotors or vacuum systems of the surgical consoles to an eye treatment handpiece, with the flow network conduit of the cassette being disposable to avoid cross-contamination between different patients.

To provide surgeons with the benefits of vacuum-based and/or displacement-based aspiration flows as appropriate for a particular procedure or portion of a procedure, it may be desirable to include both peristaltic pump drive components and a vacuum system in a single eye treatment console. Unfortunately, as eye treatment consoles get more complex, the challenge of accurately and quickly coupling a probe and appropriate cassette to an eye surgery console may increase significantly. Increased difficulties and challenges in accurately and appropriately preparing an eye treatment system for treatment of a particular patient may decrease the number of patients who will benefit from treatments from each system, and might also increase the possibility of errors or injury to a patient.

In light of the above, it would be advantageous to provide improved devices, systems, and methods for eye surgery. It would be particularly advantageous if these improvements allowed system users to configure an eye treatment system quickly, accurately, and securely, without requiring the surgical staff to manually apply excessive force and without subjecting the various interfacing components to unnecessary strains, torques, or the like. It would be particularly advantageous if mounting of a cassette onto a console could be performed easily and securely while the cassette is supported by a single hand.

BRIEF SUMMARY OF THE INVENTION

The invention generally provides improved devices, systems, and methods for mounting a cassette onto a surgical system console, often to couple the console to an eye treatment probe via a surgical fluid conduit network of the cassette. In some embodiments, receptacle surfaces of the console are driven with an axial translation linkage to mount the cassette. At least some of the translation surfaces may translate, without rotation, along an axis that is angled relative to a translation axis of the cassette, while optionally inhibiting, or render unnecessary, rotation of the cassette about all rotational axes. Interfaces between the various fluid network elements of the cassette and console components may also be provided, including a pressure sensor which slides relative to a cassette body, typically by engagement with an alignment surface of the console. Multiple peristaltic drives may include drive rotors that rotate about a common axis to facilitate alignment and mounting of the cassette. An integrated tight-tolerance mount of the console may support and position a plurality of the console components, allowing these components (and the integrated mount structure) to be assembled into the console as a unit. An axially compressibly mounted vacuum connector of the console seals against a chamfered vacuum coupler of the cassette. Exemplary surgical systems can provide an easy, positive mounting with a relatively high (often over 15 pounds) engagement force between the cassette and console with a single-hand cassette mounting process. Because the cassette may be drawn in, without the necessity of rotation in any axis, alignment between engaging elements of the cassette and console may be more precisely controlled.

In a first aspect, the invention provides an eye treatment system comprising an eye treatment probe and a console. The console may include a console support structure and a plurality of cassette receptacle surfaces defining a cassette receptacle. An axial translation linkage may couple the cassette receptacle to the support structure so that at least some of the cassette receptacle surfaces translate linearly along a first axis. A cassette may also be included with the cassette configured to couple the console with the probe. The cassette can have a plurality of positioning surfaces oriented for engagement by the receptacle surfaces, and the console may be configured to draw the cassette toward the console along a second axis that is disposed at an angle relative to the first axis.

Engagement between the positioning surfaces of the cassette and the receptacle surfaces of the console may optionally inhibit rotation of the cassette as the cassette translates with the receptacle. The angle between the axes may be between about 10 and about 30 degrees, often being about 20 degrees. The console will often include console components that are supported by the console support structure, and the components may each have an interface. The cassette may include a cassette body having a thickness along the translation axis (when the cassette is positioned for mounting onto the console), as well as a height and width. The cassette body will typically include the positioning surfaces and will have a plurality of cassette fluid network elements, each element having an associated interface. The interfaces of the cassette can be distributed across the height and width of the cassette body. Translation of the linkage of the console from a first (typically non-mounted) receptacle location to a second (typically mounted) location effects axial translation of each of the plurality of cassette element interfaces along the axis into engagement with a corresponding component interface of the console. Typical interfaces of the console and cassette may include (for example) an irrigation fluid valve interface for controlling and/or modulating irrigation fluid from the probe into the eye, As aspiration pump selection valve for selecting different aspiration pumps, an aspiration fluid drive interface for withdrawing fluid from the eye through the probe, an aspiration fluid pressure sensor interface for measuring and transmitting a pressure from along the surgical fluid network, an aspiration fluid reservoir drain drive for emptying a holding tank of the cassette, an aspiration fluid reservoir vacuum conduit interface for applying and/or controlling a level of vacuum within a holding tank of the cassette, a vent valve interface for venting irrigation fluid or atmospheric pressure into the aspiration pathway, and/or an aspiration fluid reservoir drain indicator interface for detecting when the aspiration tank is sufficiently filled that it should be drained. Many systems will include two or more of these listed interfaces, often including three of these interfaces, with exemplary embodiments including four, five, or all of these interfaces.

In many embodiments, an actuator of the console will drivingly engage the axial linkage. The actuator may effect translation of the receptacle and the cassette may engage the console with an engagement force of over about ten pounds when the cassette is fully mounted to the console, the engagement force often being over about twenty pounds, and optionally being about thirty pounds. To provide these relatively high compressive engagement forces (which can help maintain secure and often sealed engagement between the components of the console and fluid network elements of the cassette) without requiring the surgical staff to manually apply these forces while maintaining accurate alignment, the actuator can both move the receptacle and cause it to contract laterally, orienting the cassette with greater and greater accuracy as the interfaces engage. In exemplary embodiments, a first portion of the axial translation linkage can move some of the receptacle surfaces along the first axis while another portion of the axial translation linkage moves other receptacle surfaces along a third axis 125 (as shown in FIG. 4B), for example, to gradually squeeze the cassette. Along with being used to draw the cassette into a mounted position, the receptacle surfaces and actuator may also be used to disengage the console, such as through the use of receptacle surfaces inside C-channels that are only slightly wider than flanges of the cassette. After use of the cassette is complete, the cassette can then be ejected by moving the C-channels away from the console in response to an eject command.

Exemplary systems employ an automated drive and latching mechanism in which movement of the receptacle is initiated by the user manually pushing the cassette lightly against the receptacle surfaces. Imposing a slight delay while the user manually moves the receptacle surfaces a slight distance before energizing the actuator and translating the axial linkage may provide the user with a tactile feedback of positive alignment and a good cassette mounting feel. The exemplary axial linkage comprises a plurality of shafts that slide in associated guides, with the receptacle including C-channels supported by the shafts so that the channels slide over associated flanges of the cassette as the linkage moves. Angling of the sliding shafts relative to the mounting axis thus effects movement of the channels both along the mounting axis and over the flanges. The shafts may be coupled to the actuator by a CAM and roller arrangement.

In another aspect, the invention provides an eye treatment cassette for use in coupling an eye treatment probe with an eye treatment console. The console has a console support structure, a plurality of cassette receptacle surfaces defining a cassette receptacle, and an axial translation linkage coupling the cassette receptacle to the console so that the cassette receptacle surfaces translate axially without rotation. The cassette comprises a cassette body having a plurality of positioning surfaces configured for slidingly engaging the receptacle surface as the cassette translates axially with the receptacle. Optionally, the positioning surfaces may be slidingly received in channels of the receptacle during translation, with the channels fittingly receiving the positioning surfaces therein so as to inhibit undesirable movement or rotation of the cassette.

In another aspect, the invention provides an eye treatment cassette for use in coupling an eye treatment probe with an eye treatment console. The console has a console support structure, a plurality of cassette receptacle surfaces defining a cassette receptacle, and an axial translation linkage coupling the cassette receptacle to the console so that the cassette receptacle surfaces translate axially. The cassette comprises a cassette body having a plurality of positioning surfaces configured for engaging the receptacle surfaces so as to inhibit, or render unnecessary, rotation of the cassette as the cassette translates axially with the receptacle.

The cassette body will typically comprise a molded polymer structure, and the cassette positioning surfaces may include at least one axial positioning surface for positioning the cassette along the axis. The axial positioning surface(s) may extend across the height and width of the cassette. Lateral positioning surfaces may comprise four radiused corner surfaces of the cassette body, each of the corners comprising a roughly ¼ cylinder having an axis that extends along the mounting axis. The exemplary corner surfaces may include protruding ribs. A plurality of retention surfaces may protrude laterally along a width of the cassette and may be oriented away from the console when the cassette is mounted thereon. For example, the lateral retention surfaces may comprise or be positioned on flanges that extend along the lateral width of the cassette body, with the flanges being suitable for latching to the console with C-channels or the like.

In another aspect, the invention provides an eye treatment system comprising an eye treatment probe and an eye treatment console. The console has a receptacle, a pressure detection surface, and an alignment surface. A cassette is configured for coupling the probe with the console The cassette has a cassette body that is fittingly receivable by the receptacle. A pressure sensor is moveably supported by the cassette body. The pressure sensor has a pressure transmitting surface and a sensor positioning surface. The sensor positioning surface of the sensor is configured to engage the alignment surface of the console when the cassette is mounted to the console so as to move the sensor relative to the cassette body and into alignment with the detection surface of the console.

In a related aspect, the invention provides a method for assembly of an eye treatment system. The method compresses moving a sensor relative to an eye treatment cassette body and into alignment with an eye treatment console by engagement between a sensor positioning surface of the sensor and an alignment surface of the console. The cassette body supports the sensor. An eye treatment probe is coupled with an eye treatment console by mounting the cassette to the eye treatment console, often after alignment of the sensor with the alignment surface of the console.

In another aspect, the invention provides an eye treatment system comprising an eye treatment probe. A console having a cassette receptacle, a vacuum coupler exposed to the receptacle, and a vacuum source in fluid communication with the vacuum coupler is also provided. The vacuum coupler of the receptacle comprises a deformable sealing body disposed circumferentially about an axis. The sealing body is resiliently movable along the axis. The cassette has a cassette body that is fittingly receivable by the receptacle of the console. The cassette also includes a vacuum coupler that's configured for fluid communication with the probe. The vacuum coupler of the cassette includes a tubular body that has a tubular axis and an engaging surface around the tubular axis. The engaging surface tapers radially along the tubular axis so as to reposition and seal against the sealing body of the vacuum coupler of the console when the cassette is mounted.

In another aspect, the invention provides an eye treatment system comprising an eye treatment probe and a console having a cassette receptacle and a fluid drive system. The fluid drive system includes a first peristaltic drive rotor and a second peristaltic drive rotor the first and second drive rotors are exposed to the receptacle and are substantially coaxial. A cassette includes a cassette body having cassette positioning surfaces for fittingly engaging the receptacle. A fluid pathway network of the cassette couples the fluid drive system of the console with the probe. The network has a first resilient tubing segment and a second resilient tubing segment. The first and second tubing segments are configured for peristaltic driving engagement by the first and second rotors, respectively, when the cassette is mounted to the console.

In another aspect, the invention provides an eye treatment system comprising an eye treatment probe and a console having a console receptacle and an integrated mount structure. The integrated mount structure includes two or more apertures. The console also includes two or more console components, with the console components including two or more of: a first valve actuator, a second valve actuator, a vacuum coupler, and/or a pressure sensor coupler. Each console component is fittingly mounted in an associated aperture. The integrated mount structure, with the two or more components supported thereby, can be mounted in the support structure of the console as a unit. The eye treatment system also includes a cassette having a cassette body with positioning surfaces for fittingly engaging the receptacle. A fluid pathway network includes two or more cassette network elements. The elements may include a first valve portion, a second valve portion, a vacuum coupler, and/or a pressure sensor. The elements are configured for interfacing with associated components of the console when the cassette body is received by the receptacle.

BRIEF DESCRIPTION OF THE DRAWINGS

FIG. 2 schematically illustrates a cassette having a surgical fluid pathway network for use in the system of FIG. 1, with elements of the network shown with corresponding components of the console that interface with the cassette.

FIG. 3A is a perspective view similar to that of FIG. 3 in which the cassette is mounted to the console and constrained within the receptacle.

FIG. 4 is a rear perspective view showing the axial translation linkage of the console, along with some of the surrounding support structure of the console and the rear portions of some of the console components that interface with the cassette.

FIGS. 4A-4D illustrate an exemplary axial translation linkage and components thereof.

FIG. 5 is a perspective view of an exemplary surgical fluid cassette for use in the system and method of FIG. 1.

FIGS. 5A and 5B illustrate a back or interface surface of the cassette of FIG. 5, showing the fluid pathway elements assembled within the cassette body (in FIG. 5A) and in an exploded format (in FIG. 5B).

FIG. 8 is a perspective view illustrating an exemplary pressure sensor assembly of the cassette.

FIG. 8B is a perspective view showing structures of the cassette body which snap onto the pressure sensor assembly of FIG. 8, with the cassette body allowing sliding lateral motion of the sensor.

DETAILED DESCRIPTION OF THE INVENTION

The present invention generally provides improved devices, systems, and methods for surgical treatment. The devices, systems, and methods are generally directed to surgical consoles that incorporate a cassette, for example a fluidics cassette configured to couple the console to a surgical probe or handpiece. Exemplary embodiments provide improved techniques for coupling an eye treatment probe to an eye treatment console by mounting a cassette to the console.

The cassette may include a surgical fluid network, and mounting of the cassette to the console allows various network elements of the cassette to interface with corresponding components of the console. For example, the fluid network of the cassette may include resiliently deformable tubing, a pressure sensor, a holding tank or chamber, and the like. A cassette body may constrain a segment of the tubing in an arcuate configuration, so that when the cassette is mounted to the console a peristaltic drive rotor of the console engages the arc segment of tubing. This allows positive displacement pumping of aspiration fluid from the eye, through the probe, and into a waste receptacle or holding tank. A plurality of peristaltic pumps may be included, with one providing controlled aspiration and the other draining a holding tank or the like. Other segments or portions of the resilient tubing of the cassette may be engaged by valve actuators of the console so as to control irrigation and aspiration fluid into and out of the eye via the probe. Many of these interfacing console components and cassette elements may benefit from significant engagement forces to provide robust, accurately aligned, and/ or sealed interfacing therebetween.

While embodiments of the present systems may employ manual force to bring the various fluid network elements of the cassette into engagement with the corresponding console components exemplary embodiments will often include a motorized drive linkage that helps move the cassette to the mounted configuration. Many of the interfacing console components benefit from accurately aligned axial movement of the cassette to the mounted position, so that a receptacle of the console may engage positioning surfaces of the cassette so as to inhibit, or render unnecessary, rotation of the cassette during the mounting process. While some embodiments may employ a rotary cassette latching mechanism, maintaining axial movement of the cassette, thus rendering any rotation of the cassette unnecessary, may advantageously limit the angular misalignment between the interfacing structures, potentially providing better sealing or engagement between mating elements and decreasing the stresses and/or undesirable motions between these corresponding structures.

Figure 1:
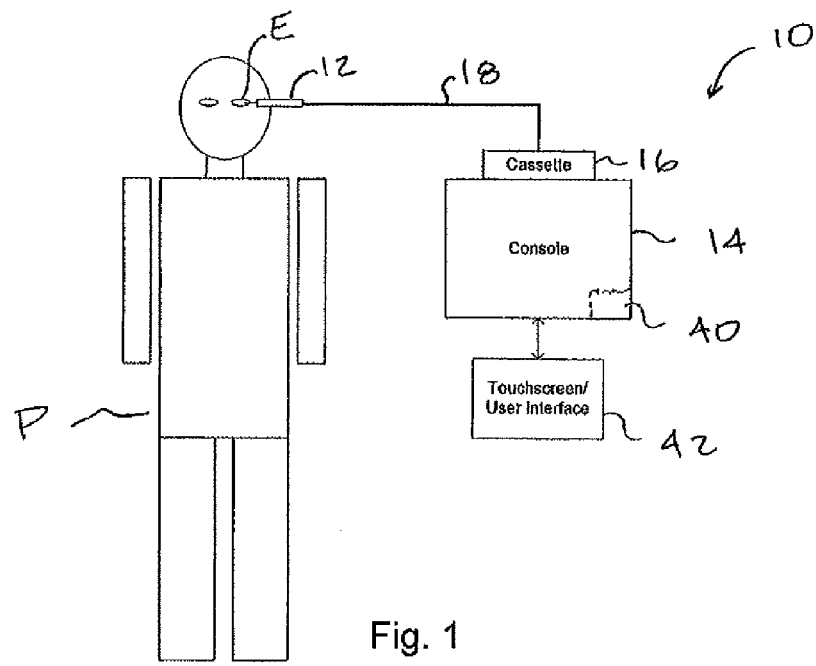
FIG. 1 schematically illustrates an eye treatment system in which a cassette couples an eye treatment probe with an eye treatment console.

Referring now to FIG. 1, a system 10 for treating an eye E of a patient P generally includes an eye treatment probe handpiece 12 coupled to a console 14 by a cassette 16. Handpiece 12 generally includes a handle for manually manipulating and supporting an insertable probe tip. The probe tip has a distal end which is insertable into the eye, with one or more lumens in the probe tip allowing irrigation fluid to flow from the console 14 and/or cassette 16 into the eye. Aspiration fluid may also be withdrawn through a lumen of the probe tip, with the console 14 and cassette 16 generally including a vacuum aspiration source, a positive displacement aspiration pump, or both to help withdraw and control a flow of surgical fluids into and out of eye E As the surgical fluids may include biological materials that should not be transferred between patients, cassette 16 will often comprise a disposable (or alternatively, sterilizable) structure, with the surgical fluids being transmitted through flexible conduits 18 of the cassette that avoid direct contact in between those fluids and the components of console 14.

When a distal end of the probe tip of handpiece 12 is inserted into an eye E, for example, for removal of a lens of a patient with cataracts, an electrical conductor and/or pneumatic line (not shown) may supply energy from console 14 to an ultrasound transmitter of the handpiece, a cutter mechanism, or the like. Alternatively, the handpiece 12 may be configured as an I/A or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

As to avoid cross-contamination between patients without incurring excessive expenditures for each procedure, cassette 16 and its flexible conduit 18 may be disposable. Alternatively, the flexible conduit or tubing may be disposable, with the cassette body and/or other structures of the cassette being sterilizable. Regardless, the disposable components of the cassette are typically configured for use with a single patient, and may not be suitable for sterilization. The cassette will interface with reusable (and often quite expensive) components of console 14, including peristaltic pump rollers, a Venturi or other vacuum source, a controller 40, and the like.

Controller 40 may include an embedded microcontroller and/or many of the components common to a personal computer, such as a processor, data bus, a memory, input and/or output devices (including a touch screen user interface 42), and the like. Controller 40 Will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet™, a wireless network, or the like. Along with programming code, controller 40 may include stored data for implementing the methods described herein, and may generate and/or store data that records perimeters with corresponding to the treatment of one or more patients. Many components of console 14 may be found in or modified from known commercial phacoemulsification systems from Advanced Medical Optics Inc. of Santa Ana, Calif.; Alcon Manufacturing, Ltd. of Ft. Worth, Tex., Bausch and Lomb of Rochester, N.Y., and other suppliers.

Figure 2A:
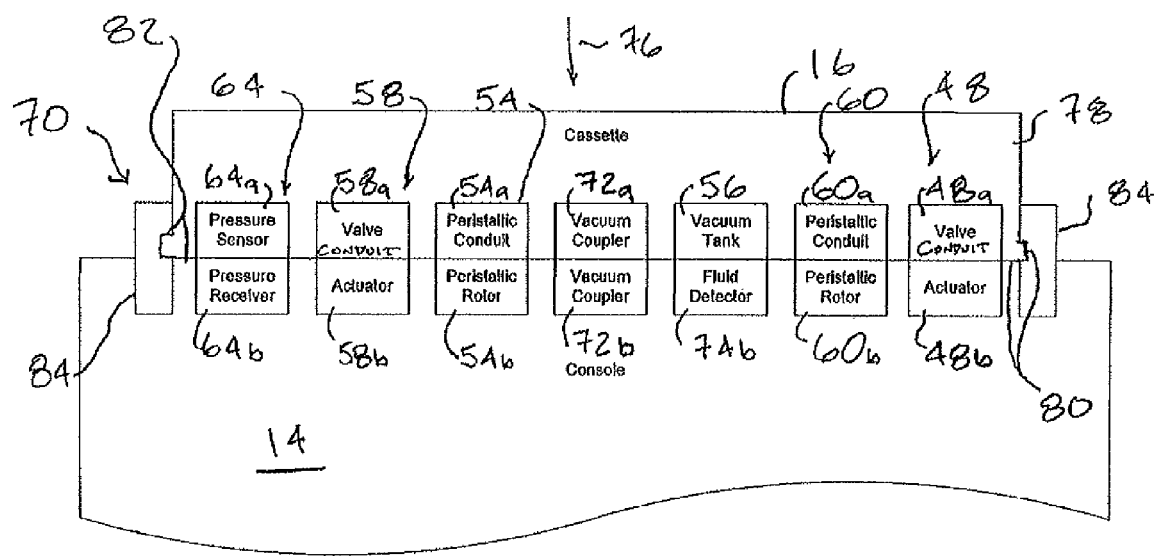
FIG. 2A schematically illustrates elements of the cassette and console of FIG. 1.

Referring now to FIGS. 1, 2 and 2A, components of the aspiration and irrigation fluid flow networks of system 10 are shown in more detail. FIG. 2 generally highlights the surgical aspiration and irrigation fluid control elements included within the cassette 16, with the irrigation components often being relatively straightforward. An irrigation source 46 of the console optionally provides irrigation fluid pressure control by relying at least in part on a gravity pressure head that varies with a height of an irrigation fluid bag or the like. An irrigation on/off pinch valve 48 may generally include a short segment of a flexible conduit of cassette 16, which can be engaged and actuated by an actuator of the console, with a surface of the cassette body often being disposed opposite the actuator to facilitate closure of the conduit lumen. Alternative irrigation flow systems may include positive displacement pumps, alternative fluid pressurization drive systems, fluid pressure or flow modulating valves, and/or the like.

The aspiration flow network 50 generally provides an aspiration flow path 52 that can couple an aspiration port in the tip of handpiece 12 to either a peristaltic pump 54 and/or a holding tank 56. Fluid aspirated through the handpiece may be contained in holding tank 56 regardless of whether the aspiration flow is induced by peristaltic pump 54 or the vacuum applied to the holding tank. When valve 58 is closed and peristaltic pump 54 is in operation, pumping of the aspiration flow may generally be directed by the peristaltic pump, independent of the pressure in the holding tank 56. Conversely, when peristaltic pump 54 is off, flow through the peristaltic pump may be halted by pinching of the elastomeric tubing arc of the peristaltic pump by one or more of the individual rollers of the peristaltic pump rotor. Hence, any aspiration fluid drawn into the aspiration network when peristaltic pump 54 is off will typically involve the opening of a selector control valve 58 so that the aspiration port of the probe is in fluid communication with the holding tank. Alternatively, communication with the vacuum source 44 may be accomplished by disengaging the peristaltic probe drive from the elastomeric tubing. The pressure within tank 56 may be maintained at a controlled vacuum level, often at a fixed vacuum level, by a vacuum system 44 of the console. The vacuum system 44 may comprise a Venturi pump, a rotary vane pump, a vacuum source, or the like. Aspiration fluid that drains into holding tank 56 may be removed by a peristaltic drain pump 60 and directed to a disposal fluid collection bag 62. Vacuum pressure at the surgical handpiece may be maintained within a desired range through control of the fluid level in the holding tank.

In more detail, the operation of aspiration flow network 50 can be understood by first considering the flow when valve 58 is closed. In this mode, peristaltic pump 54 draws fluid directly from handpiece 12, with a positive displacement peristaltic pump flow rate being controlled by the system controller 40 (see FIG. 1). To determine the appropriate flow rate, the level of vacuum within the aspiration flow network may be identified in part with reference to a pressure or vacuum sensor 64 disposed along the aspiration flow network 50 between peristaltic pump 54 and handpiece 12. This allows the system to detect and adjust for temporary occlusions of the handpiece and the like. While the aspiration material flows through holding tank 56 and eventually into collection bag 62, the holding tank pressure may have little or no effect on the flow rate in this mode.

When peristaltic pump 54 is not in operation, rotation of the peristaltic pump is inhibited and the rotors of the peristaltic pump pinch the arcuate resilient tubing of the probe so as to block aspiration flow. Material may then be drawn into the aspiration port of handpiece 12 by opening selector valve 58 and operation of the venture pump 57 or other vacuum source 44. When valve 58 is open, the aspiration port draws fluid therein based at least in part on the pressure differential between holding tank 56 and the chamber of the eye in which the fluid port is disposed. Hence, aspiration network 50 allows system 10 to operate in either peristaltic or vacuum-based pumping modes. In some embodiments, particularly when only peristaltic pumping will be used for a particular procedure, alternative cassettes may be employed, with the alternative cassette lacking a holding tank 56, selector valve 58, and the like.

Referring now to FIG. 2A, an interface 70 between cassette 16 and console 14 is schematically illustrated. Many of the fluid network structure described above regarding FIG. 2 include or make use of corresponding elements of the cassette and the console 14. For example, pressure sensor 64 may be included in a pressure sensing system which includes a pressure sensor 64a having a pressure chamber and a surface that moves in response to variations in the pressure in the chamber. Axial movement of the pressure sensor surface may be determined using a pressure receiver 64b. In the exemplary embodiments, direction of movement of the pressure sensor surface may be aligned with a mounting axis 76 of cassette 16, representing a direction of movement of the cassette during mounting of the cassette to console 14.

Similarly, selector valve 58 may make use of a resilient valve conduit 58a in the cassette 16 that is engaged by an actuator 58b of console 14. As described above, peristaltic aspiration pump 54 may include a peristaltic conduit 54a of cassette 16 engaged by a peristaltic rotor 54b of console 14, with the interface 70 effecting engagement between the conduit 54a and the peristaltic rotor 54b. A vacuum coupler 72a of cassette 16 may engage a vacuum coupler 72b of console 14 so as to allow vacuum source 44 to apply a vacuum to holding tank 56 (See FIG. 2). Holding tank 56 may be coupled to a fluid detector 74b of console 14 using a mechanical, electrical, or light fluid presence detector system so as to allow the controller 40 of console 14 to determine when it is appropriate to energize a peristaltic drain pump 60. Rather than simply detecting the presence of fluid, alternative embodiments might employ a more complex fluid level sensing system which determines a quantity or volume of fluid in the tank for purposes of selectively energizing the drain pump. Drain pump 60 includes a peristaltic conduit 60a of cassette 16 and a peristaltic rotor 60b of console 14. Irrigation valve 48 may include a resilient valve conduit 48a of cassette 16 and a valve actuator 48b of console 14.

In addition to the individual interfaces, cassette 16 will generally include a cassette body 78 with positioning surfaces 80 that engage corresponding receptacle surfaces 82 of console 14. Receptacle surfaces 82 define a receptacle that receives and positions cassette 16. At least some of receptacle surfaces 82 are supported by an axial translation linkage mechanism 84 that moves cassette 16 along axis 76 to the mounted position shown schematically in FIG. 2A.

Engagement between cassette 16 and the interfacing structures of console 14 can be understood with reference to FIGS. 3-7. Cassette 16 generally has height H and a width W which generally are greater than a thickness of the cassette along mounting axis 76, allowing the interfacing fluid pathway network elements of the cassette and corresponding components of the console to be distributed in a roughly planner configuration. In the exemplary embodiment, cassette 16 is manually supported and advanced along mounting axis 76 until positioning surfaces 80 engage and slightly deflect receptacle surfaces 82 of the console, with the receptacle surfaces here comprising C-shaped channels or C-channels 86. More specifically, the inner surfaces of the C-channels receive flanges 88 of the cassette therein, and the C-channels are then drawn towards each other and along axis 76 so as to mount the cassette to the console.

In the exemplary embodiment, a microswitch 90 detects engagement between the cassette and C-shaped channels, and initiates automatic latching after the user has manually pushed the cassette with sufficient force to cause the C-shaped channels on either side of the cassette to move on top of the cassette flanges. This delay in initiation of automatic latching gives the user tactile feedback that the cassette is properly engaged and/or aligned before the cassette is automatically drawn into the mounted position with the console, but generally does not require the user to push the cassette with more than a light force (as the C-channels are only lightly biased toward their fully extended position). Delay in initiation of automatic latching may be generated using a timing circuit of controller 40, and/or by configuring the microswitch for activation after appropriate linkage displacement. Once the automatic lathcing is initiated, an actuator drives linkage 84 applies forces to properly compress the resilient tubing and/or position the interfacing structures such as valve actuators, the pressure sensor, the peristaltic pump heads, and the like. C-channels 86 may be configured to inhibit rotation of cassette 16 during movement of the cassette by linkage 84.

Figure 3:
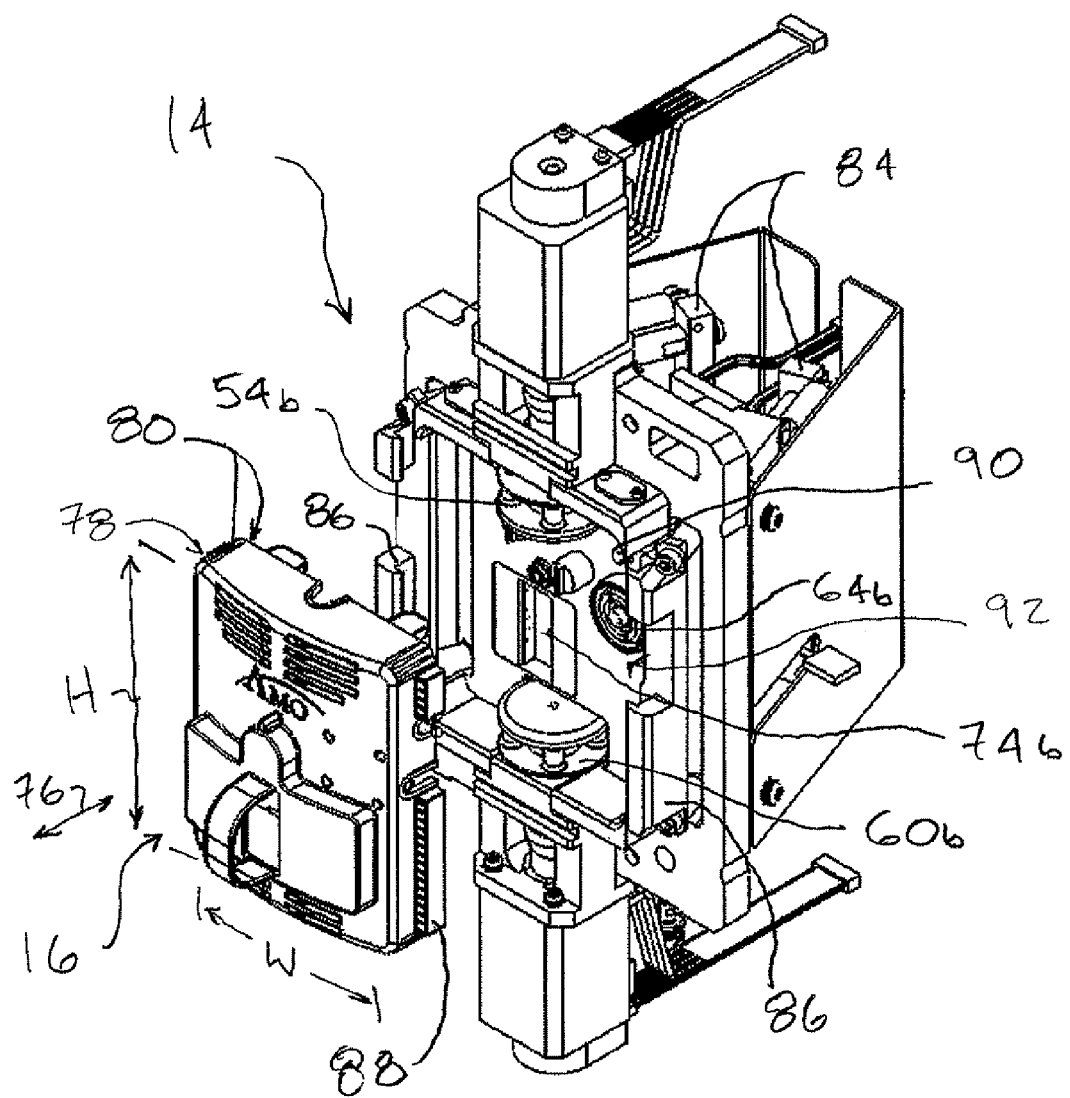
FIG. 3 is a perspective view showing an exemplary embodiment of an eye treatment cassette and a receptacle of the console for mounting the cassette, along with associated components of the console.

FIG. 3A illustrates cassette 16 mounted to console 14. The arrangement of C-channels, along with upper and lower receptacle surfaces shown in FIGS. 3 and 3A help identify an outline of receptacle 92 of the console, and some of the surrounding support structure 94 of console 14 can also be seen. Note that the flexible conduits which extend from cassette body 78 during use are omitted from FIGS. 3 and 3*a* for clarity.

Figure 3B:
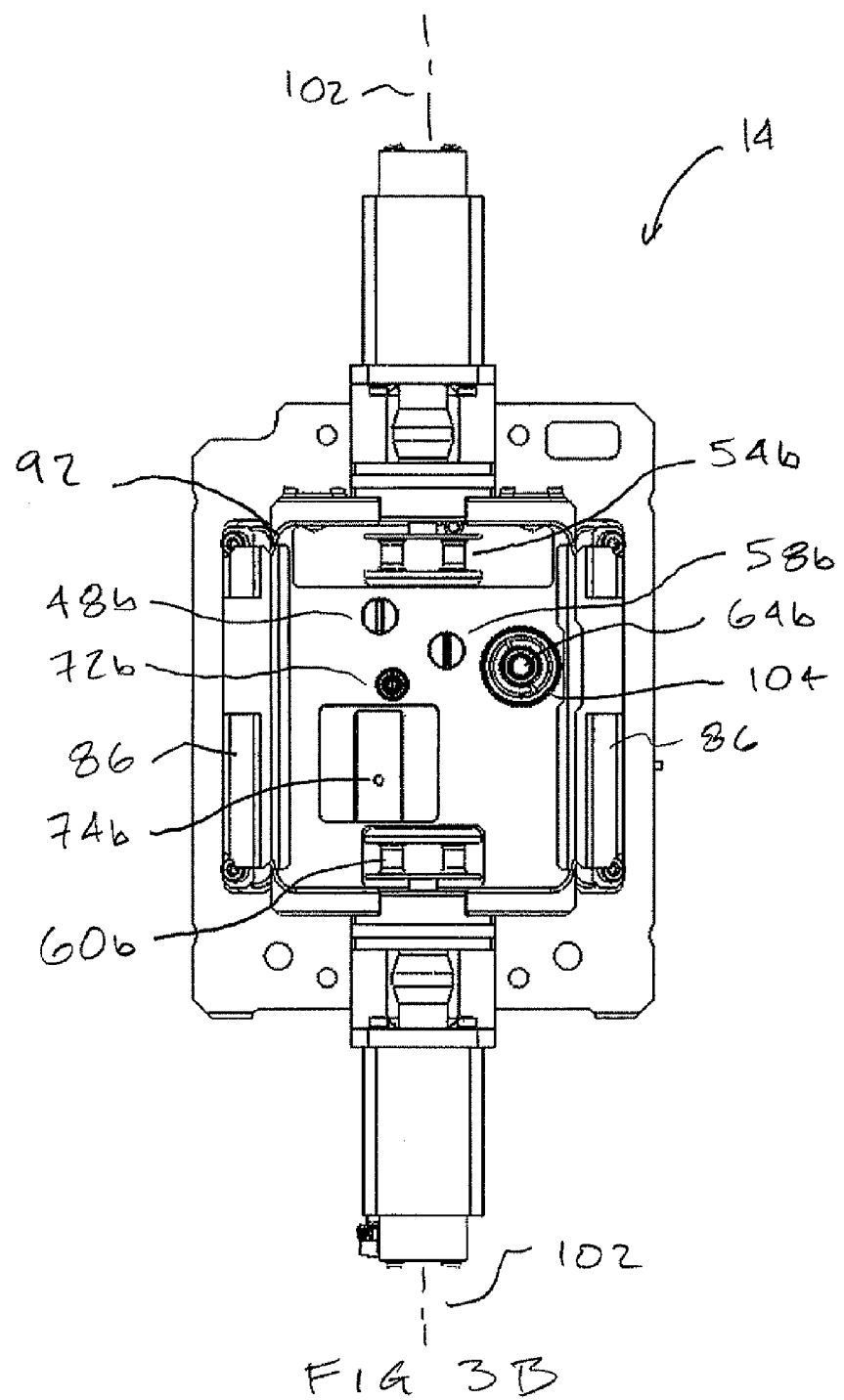
FIG. 3B is a front view showing the receptacle of the console and components of the console that interface with the cassette.

The arrangement of the components of the console 14 that are exposed to receptacle 92 for coupling of the console to cassette 16 can be seen in FIGS. 3 and 3B. Aspiration drive rotor 54*b* and drain drive rotor 60*b* rotate about a common axis 102. A protruding alignment surface 104 (seen in the form of a tubular body extending into receptacle 92) has a chamfered or tapered distal end so as to move the pressure sensor into alignment with pressure receiver 64*b*. Valve actuators 48*b* and 58*b*, vacuum coupler 72*b*, and pressure receiver 64*b* (along with alignment surface 104) may be coupled together for mounting into console 14 using an integrated support structure, as will be described below with reference to FIGS. 9*a* and 9*b*.

The exemplary axial translation linkage 84 can be understood with reference to FIGS. 4 and 4A through 4D. Linkage 84 provides driven latching of the cassette to console 14 along mounting axis 76 by energizing an actuator 112. Actuator 112 may comprise a linear drive electrical motor, a hydraulic or pneumatic piston, a vacuum piston, or the like. Regardless, the exemplary actuator 112 causes linear movement of actuator plate 114, which is coupled to a connector plate 116 and a cam roller 118 (supported by the actuator plate) and a cam surface 120 (attached to the connector plates). This arrangement allows the linear movement of actuator plate along axis 76 to induce linear movement of shafts 122 along their inclined axis 124.

Shafts 122 may be slidably restrained within guides 126 or similar such structure, so that movement of the actuator plate 114 away from the receptacle causes the C-channels 86 to move the cassette 16 toward the console and also to draw towards each other so as to capture the flange surfaces of the cassette. Movement of C-channels 86 along axes 124 may also enhance alignment of the cassette with the console as the cassette is moved to the mounted position, effectively decreasing the size of the receptacle of the console so that the positioning surfaces of the cassette are more fully constrained. Advantageously, during actuator of linkage 84, rotation of the cassette 16 is inhibited, or rendered unnecessary, by contact between the flanges and other positioning surfaces of the cassette against the inner surfaces of the C-channels 86. Additionally, the drive mechanism avoids rotating joints, both between the cassette and between the various links of linkage 84. This may help avoid rotation torques that could cause the cassette to improperly seat against the control console. In general, cassette 16 is automatically drawn into engagement with and secured to console 14 by actuator 112 when the cassette comes into contact with the surfaces of the channels 86.

Referring now to FIGS. 5, 5A, and 5B, the structure of exemplary cassette 16 may be better understood. Cassette 16 generally includes a molded polymer cassette body 78, with the cassette body defining the positioning surfaces. Alternatively, the cassette body 78 may be made of other material such as a metal, for example, a material having properties suitable for allowing the cassette to be sterilized for re-use or for making the cassette 16 inexpensive to fabricate (allowing the cassette 16 to be disposed of after a single use. Flexible conduit 18 for coupling the cassette to an irrigation fluid supply, for coupling the aspiration and irrigation flow networks to the handpiece 12, and for defining elements of the fluid networks (such as pinch valves or peristaltic arc segments) are also included with the cassette. A simple polymer fluid disposal bag 132 may be mounted to cassette body 78, with the disposal bag receiving outflow from the drain pump.

Positioning surfaces 80 are distributed around the perimeter of the interface portion of the cassette body, and/or may be more generally distributed across most of the width and height of the cassette. Elements of the surgical fluid networks, along with the rear-facing positioning surfaces 80 of cassette 16 are seen in FIGS. 5A and 5B. The structure of vacuum coupler 72*a*, as formed integrally with tank 56 can also be seen, with these structures typically optionally comprising a clear polymer material. In order to enhance sealing function, vacuum coupler 72*a* may comprise a tubular structure having a chamfered inner surface 134 and a straighter inner lumen disposed behind the chamfered surface. Alternatively or additionally, the vacuum coupler 72*a* may comprise other sealing structures or elements such as an O-ring or gasket.

Figure 6A:
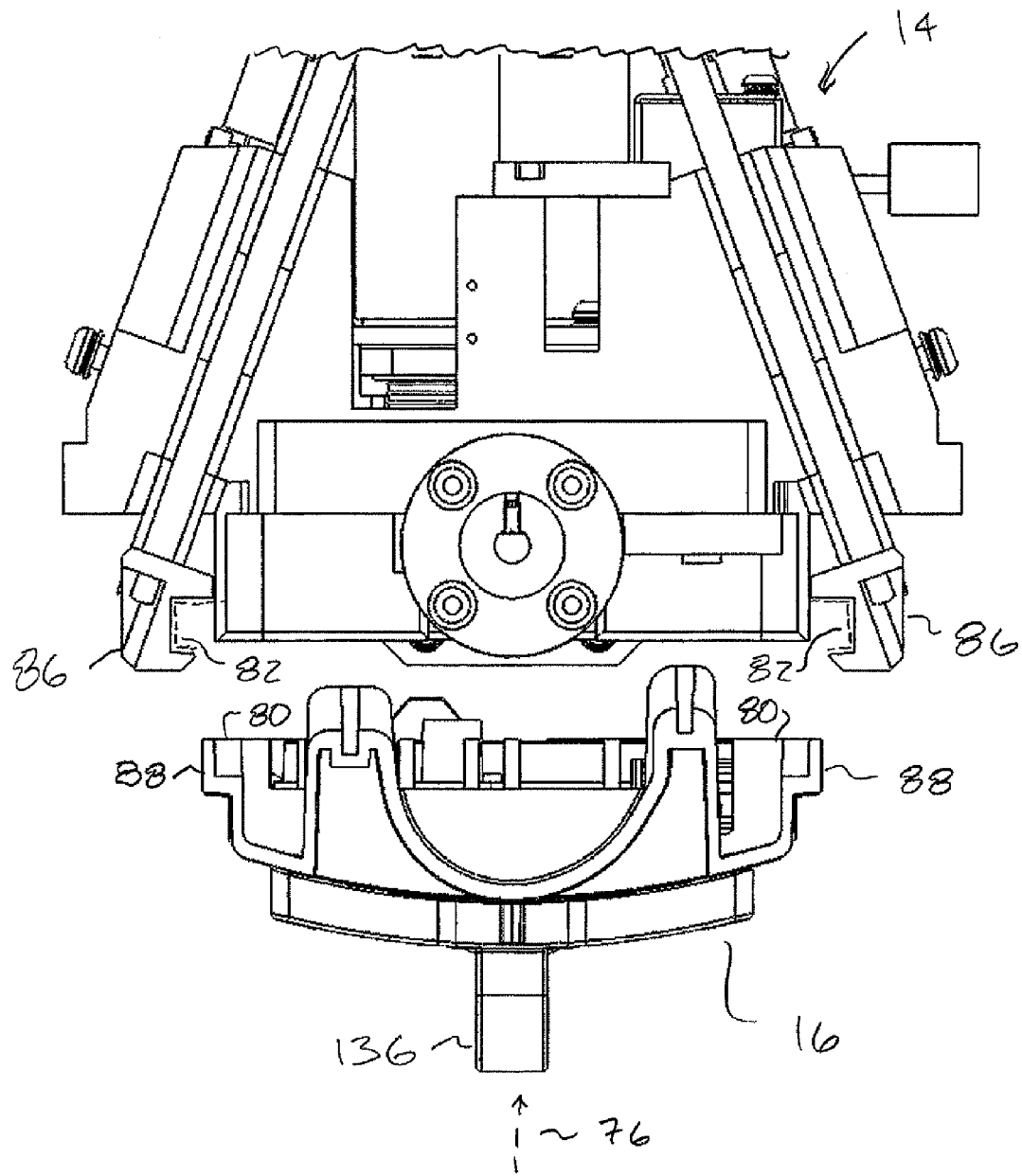
FIGS. 6A-6D are top views illustrating engagement of positioning surfaces of the cassette against receptacle surfaces of the console, along with axial actuation of the linkage to contract the receptacle, latch the cassette within the receptacle, and move the cassette axially to a mounted position.
Figure 6B:
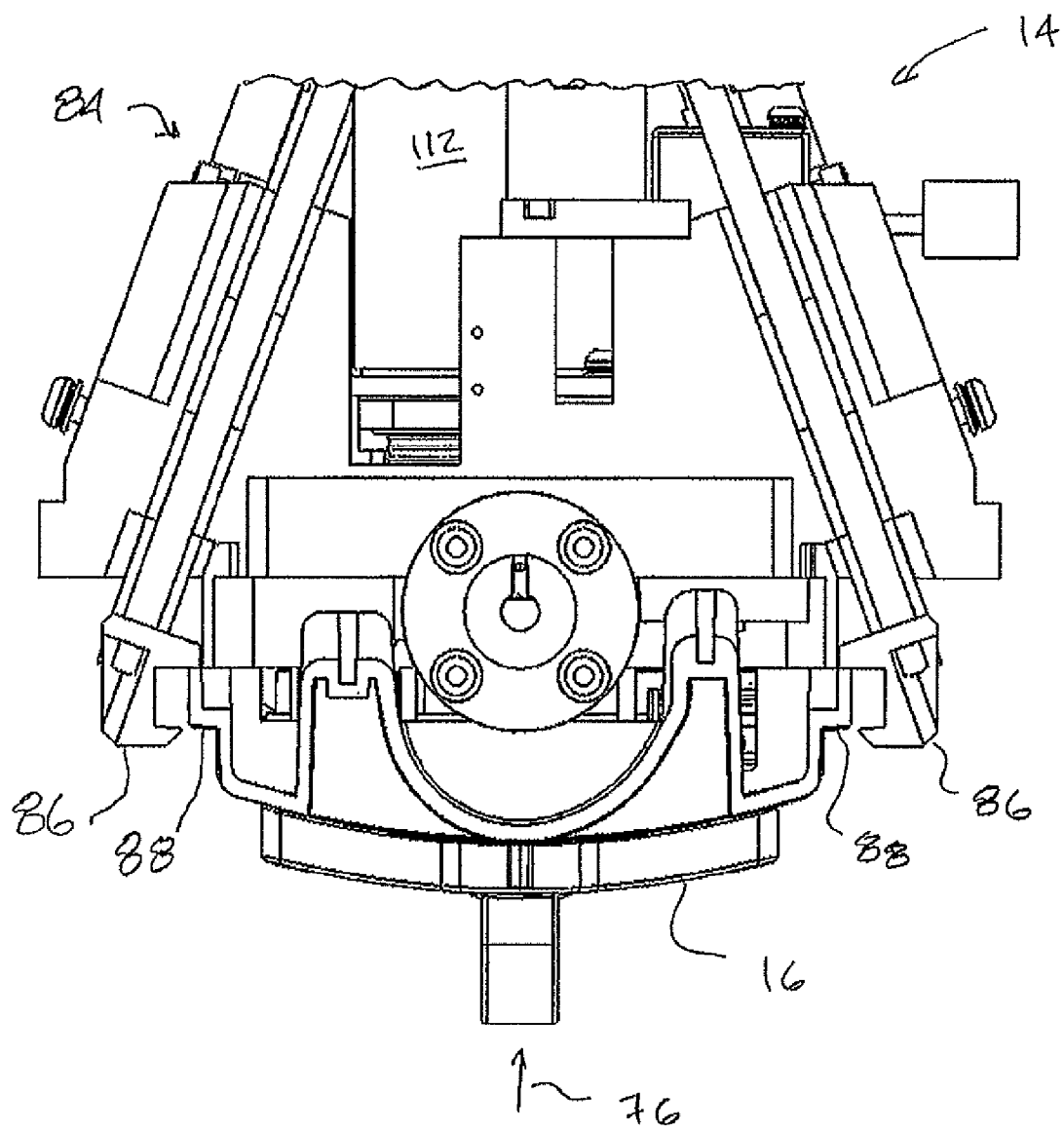
Figure 6C:
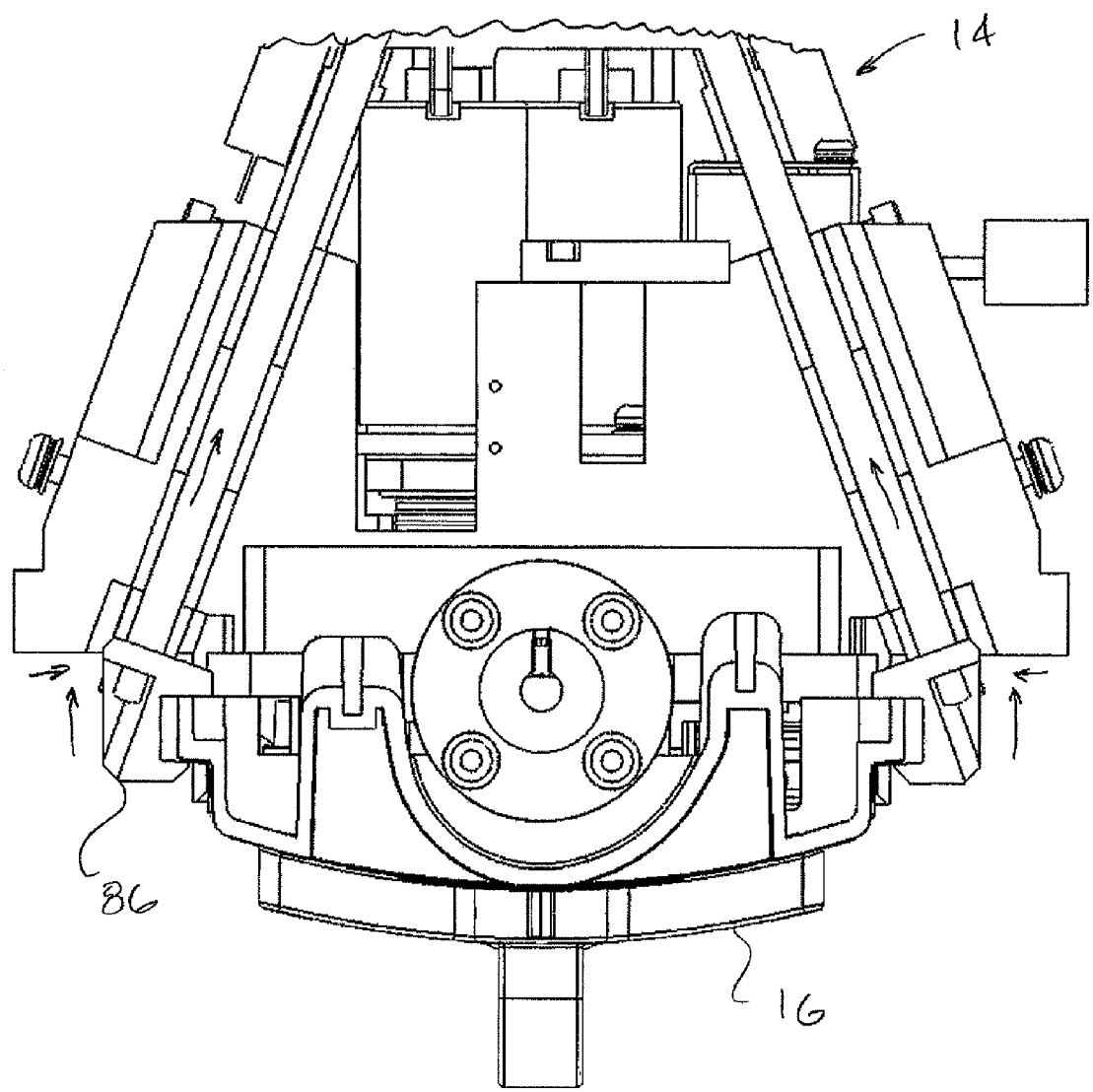
Figure 6D:
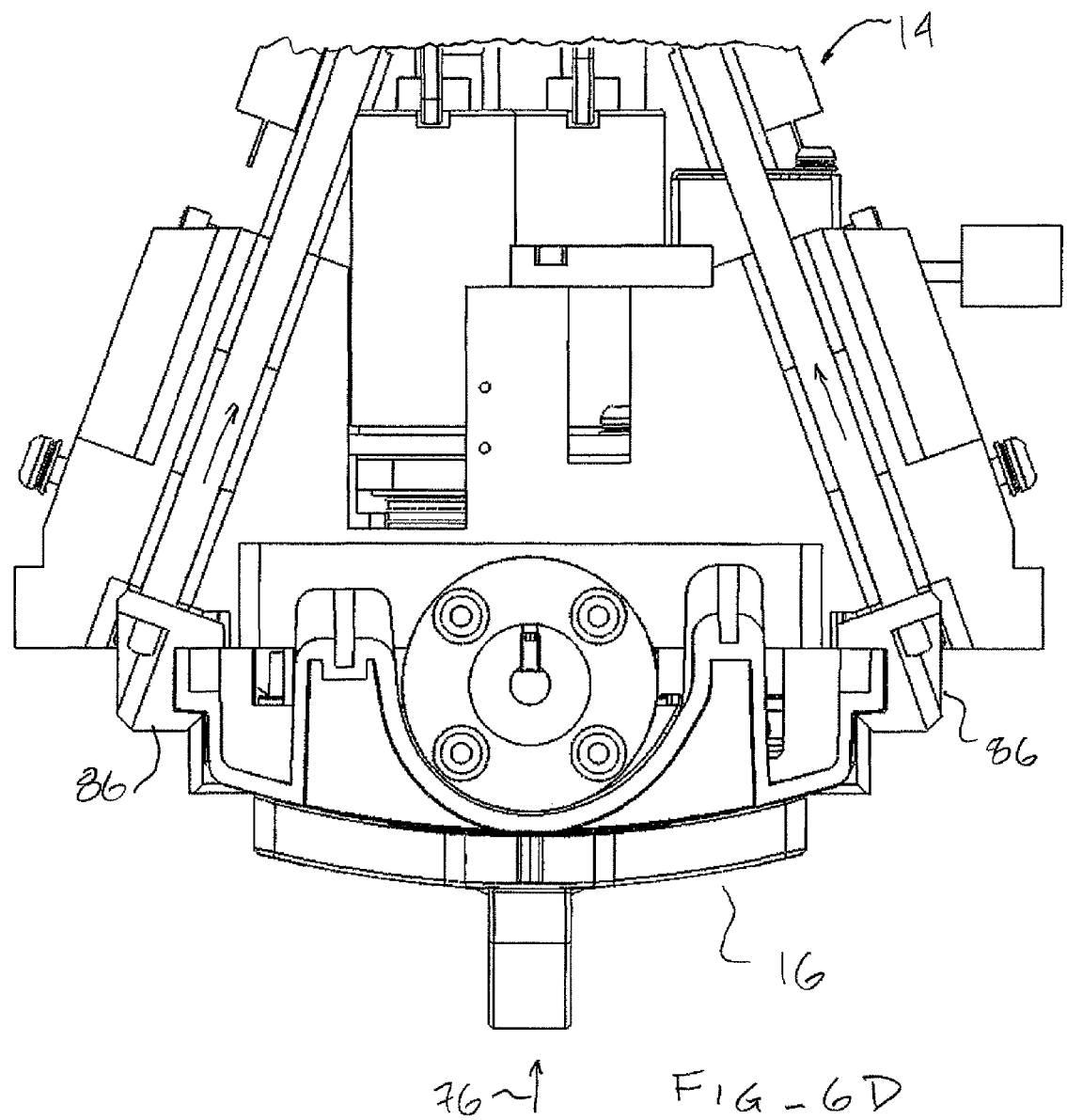

Mounting of cassette 16 onto console 14 can be more fully understood with reference to FIGS. 6A through 6C. Cassette 16 will typically be supported by a single hand that grasps handle 136 before and/or during mounting, and the cassette will generally be moved toward receptacle 82 of console 14 manually. As flanges 88 (and optionally other positioning surfaces 80 of cassette 16) engage the inner channel surfaces of channels 86 (and/or other receptacle surfaces of receptacle 82), engagement between the cassette 16 and receptacle may inhibit rotation of the cassette, allowing axial translation of the cassette along mounting axis 76 (See FIGS. 6A and 6B).

Once the cassette 16 begins to manually displace the channels 86, the cassette actuates a microswitch exposed along receptacle surfaces or coupled to the linear linkage 84. The controller 40 of console 14 may, in response, energize the actuator 112 so as to move linkage 84 and bring the receptacle and cassette 16 to the mounted position. As can be understood with reference to FIGS. 6B, 6C, and 6D, channels 86 draw cassette 16 axially along axis 76 from their fully extended configuration to the mounted position without rotation of the cassette, with the channels moving along their inclined axes so as to capture and more accurately align the cassette with the console.

Figure 7:
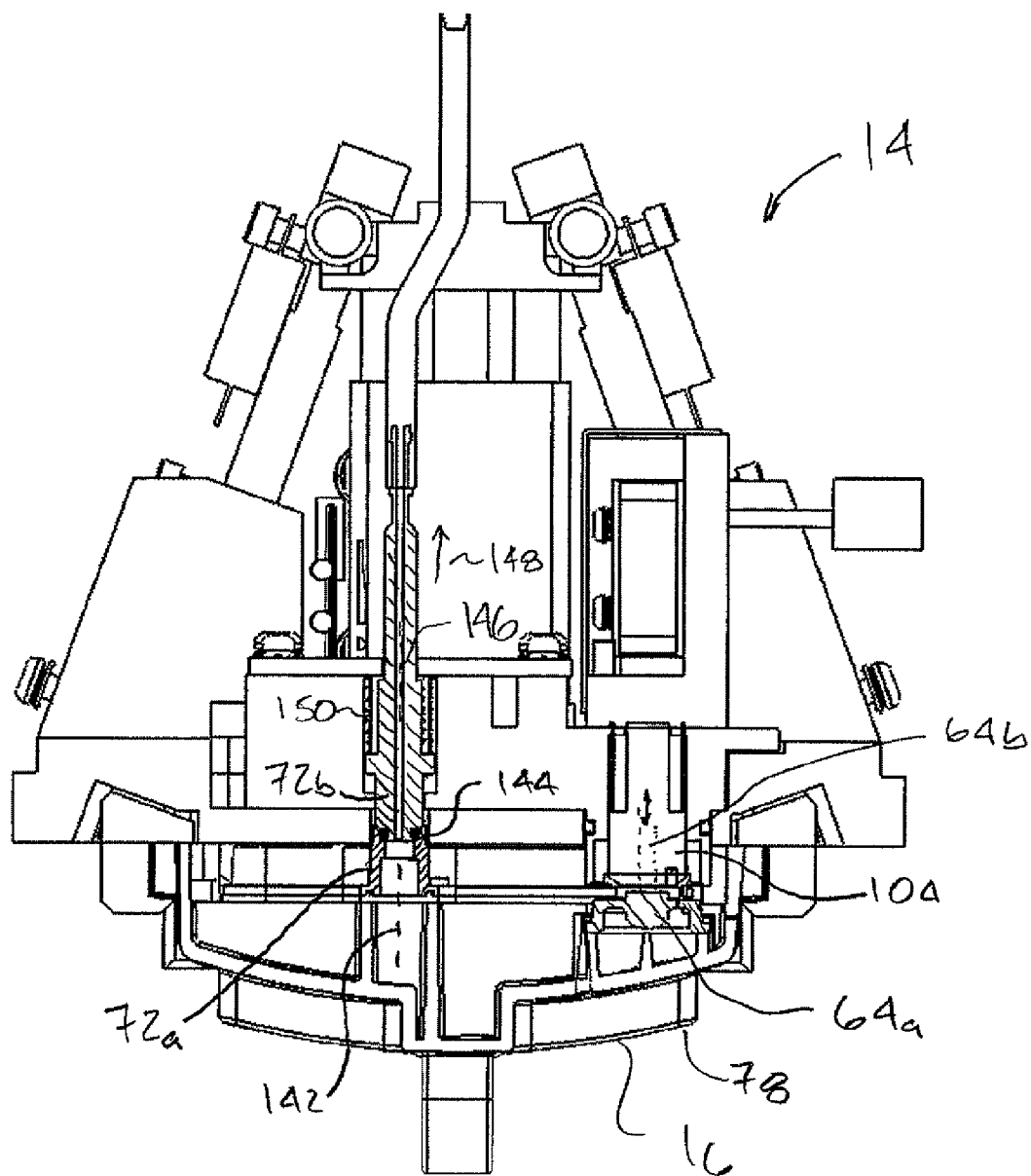
FIG. 7 is a top view showing a cassette mounted to the adjacent console structure, along with engagement of a vacuum coupler of the cassette with a vacuum coupler of the console.

Cassette 16 is seen fully mounted on console 14 in FIG. 7, which also shows engagement between the vacuum couplers 72*a*, 72*b*, and between alignment surface 104 and pressure sensor 64*a*. First addressing the vacuum coupling, vacuum coupler 72*a* of cassette 16 in the illustrated embodiment comprises a tubular body or nipple that extends toward the console about an axis 142. A distal surface of the tubular body is chamfered, so that the surface tapers radially outwardly from axis 142 going toward console 14. Vacuum coupler 72*b* preferably has a detent in which an O-ring 144 is disposed, and the vacuum coupler 72*b* is resiliently mounted to the surrounding console structure so as to accommodate sliding movement along its tubular axis 146. As cassette 16 Moves into the mounted position, the tapered surface of vacuum connector 72*a* of the cassette engages the O-ring 144 of vacuum connector 72*b*, causing axial movement of vacuum coupler 72*b* in the direction of arrow 148 and compressing a spring 150. The spring forces causes compression of the O-ring that provides a seal despite any modest axial misalignment between the vacuum couplers 72*a*, 72*b*.

Vacuum couplers 72*a*, 72*b* may be configured to facilitate a robust seal and provides enhanced fluid communication between holding tank 56 and a venturi pump or other vacuum source of console 14. By employing a vacuum connector 72b in the form of a spring loaded nipple that protrudes from console 14, and by interfacing that connector with a chamfered vacuum connector sealing surface of connector 72a, fluid coupling between the holding tank and vacuum source may be reliably and reproducibly sealed. While O-ring 144 of the protruding nipple connector 72b allows a seal to be formed even when there is slight axial misalignment between the couplers, such axial misalignment may bemay be reduced for embodiment of the present invention through the use of a latching mechanism that draws the cassette axially into the engaged position with the console.

Figure 8A:
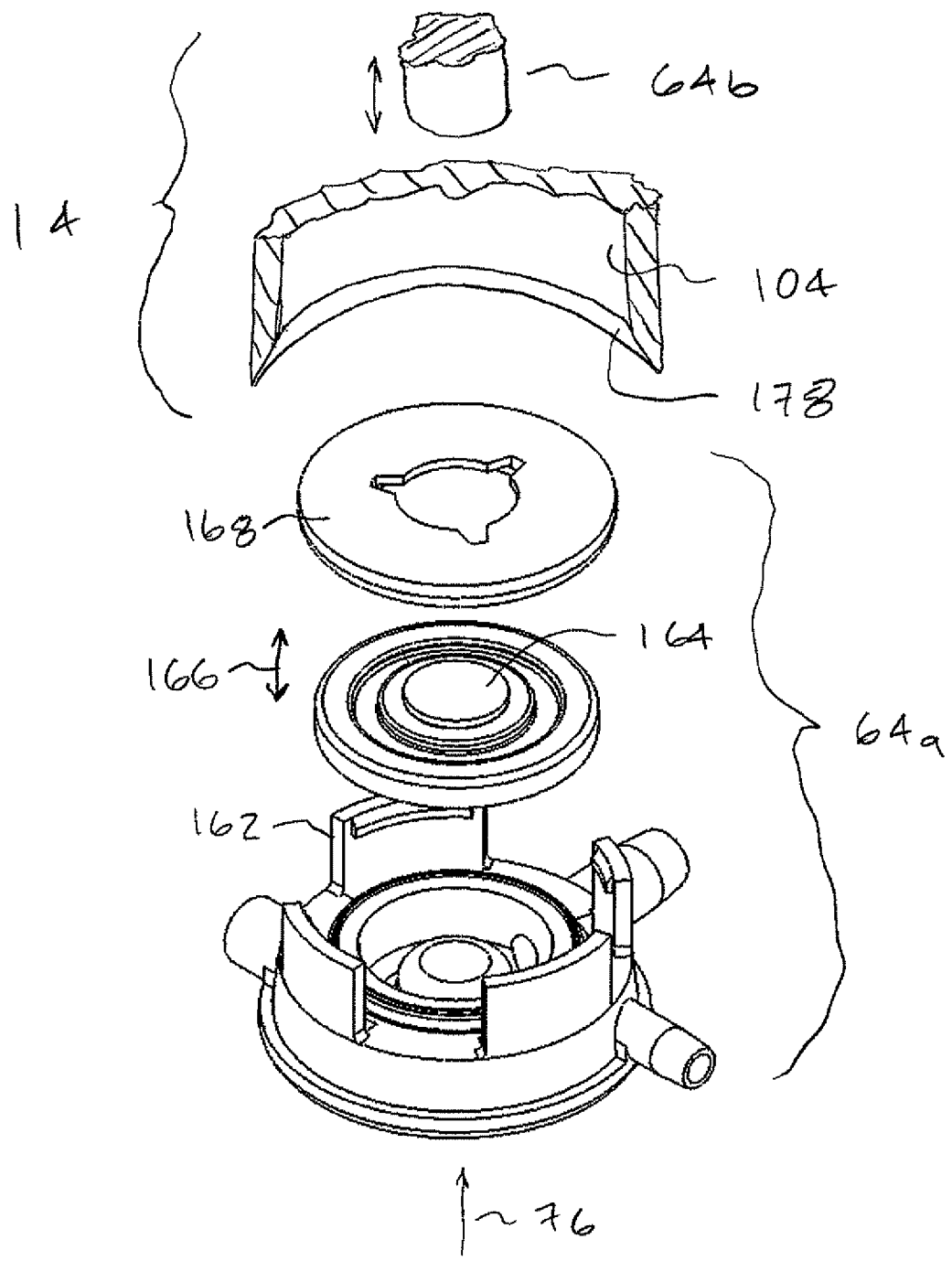
FIG. 8A is an exploded view of the pressure sensor assembly of FIG. 8, along with a chamfered tubular alignment surface of the console that moves the sensor into alignment with a pressure signal receiving or detecting structure.

The interface between pressure sensor 64a and pressure receiver 64b can be understood with reference to FIGS. 7, 8, 8A, and 8B. Referring to FIGS. 8 and 8A, sensor assembly 64a of cassette 16 includes a housing 162 that is sealed by a displaceable surface 164. Displaceable surface 164 is displaced along an axis 166 in response to pressures within the chamber of housing 162, and a lid 168 disposed over the displaceable surface allows movement of the surface along the axis.

Sensor assembly 64a includes a lower surface 170 with a chamfered flange 172. As can be understood with referenced to FIGS. 5a and 5b, lower surface 170 of sensor assembly 64a is slidably mounted to cassette 16 by snapping flange 172 past detents 174, so that the detents move back over the flange and generally hold the sensor assembly in place. The detents are spaced around sensor assembly 64a somewhat loosely, so that lower surface 170 can slide laterally (relative to axis 166) along a sensor engaging surface 176 of cassette 16.

As can be understood with reference to FIGS. 7, 8A, and 6C, as cassette 16 moves along axis 76 to the mounted position, a chamfered portion 178 of alignment surface 104 laterally moves sensor assembly 64a relative to the adjacent cassette body 78. More zspecifically, lower sensor surface 170 of sensor assembly 64a slides along sensor engaging surface 176 of cassette body 78, and although the detents 174 may continue to support the sensor relative to the cassette body, they accommodate this lateral sliding motion. As alignment surface 104 fittingly receives housing 162 therein, this sliding of the sensor relative to the adjacent cassette structure allows accurate axial alignment of the displaceable surface 164 relative to sensor receiver 64b.

Figure 9A:
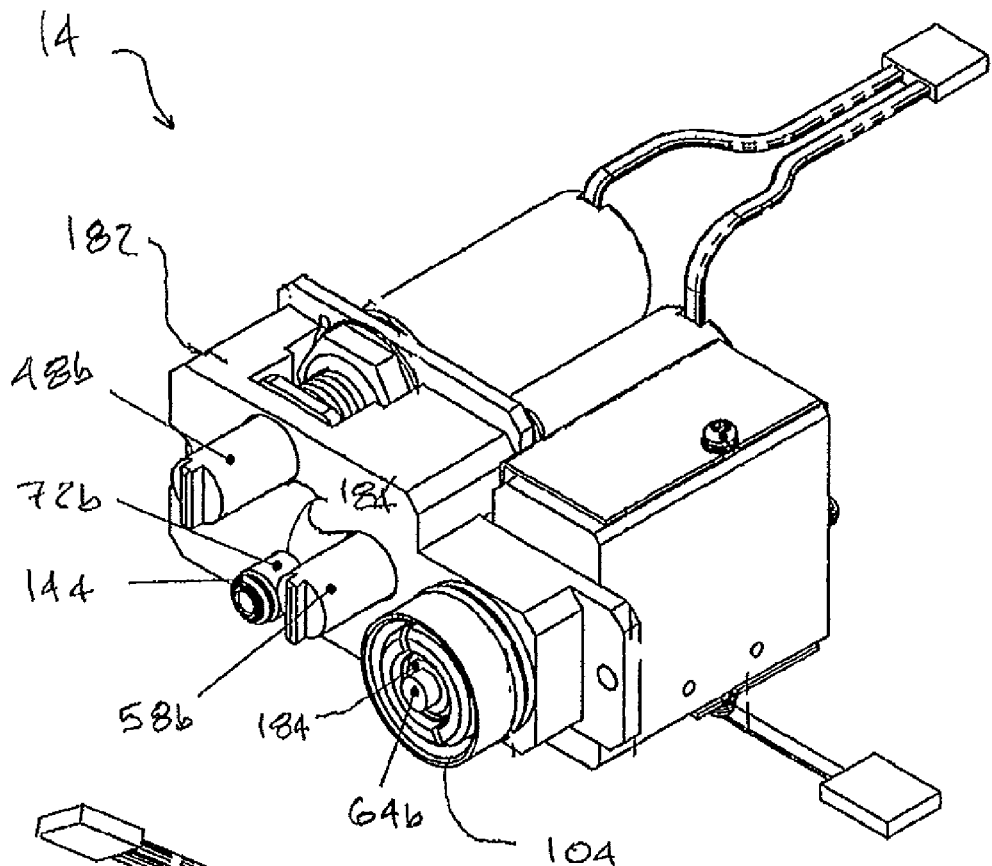
FIGS. 9A and 9B are front and rear perspective views of a unibody integral mount structure that facilitates accurate positioning of selected console components with the receptacle and cassette, and also illustrates a protruding sensor alignment surface and a protruding and resiliently moveable vacuum coupler.
Figure 9B:
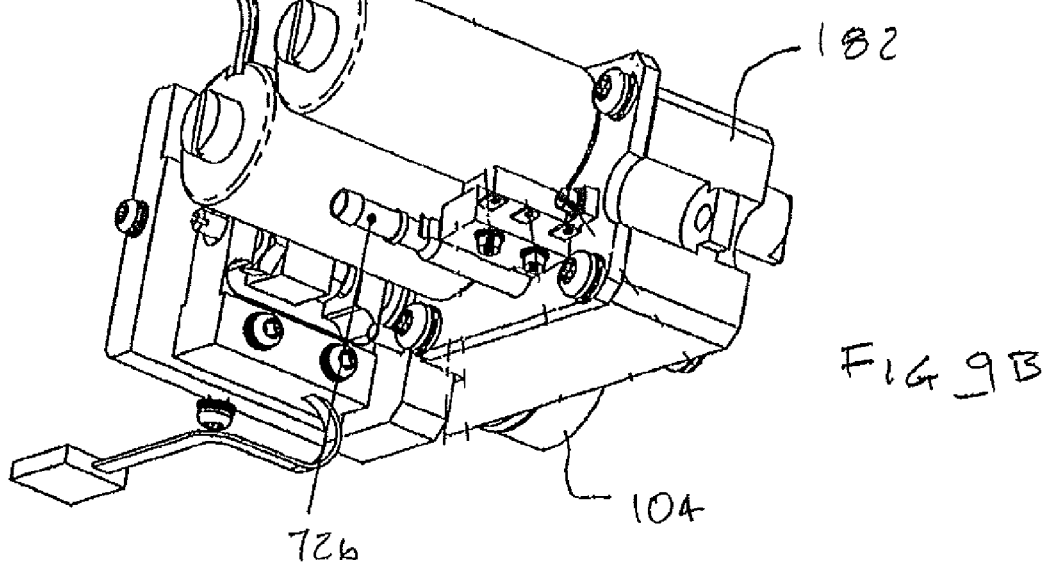

Referring now to FIGS. 9A and 9B, alignment of many of the components of console 14 that will interface with the surgical fluid network elements of the cassette may be significantly facilitated by the use of an integrated mount structure 182. Structure 182 may include a plurality of apertures 184, with each aperture fittingly receiving an associated component of console 14, such as a valve actuator 48b, 58b, a vacuum coupler 72b, a sensor receiver 64b, or the like. Structure 182 may also comprise or support protruding alignment surface 104 for (for example) laterally moving sensor 64a into alignment with sensor receiver 64b when the sensor is moved axially into engagement therewith. As structure 182 holds the associated components of console 14 in alignment with each other, these associated components may be readily aligned with the remaining structures of the console (including the cassette receptacle) by accurate positioning and mounting of structure 182 to the adjacent console support structure 94 (see FIG. 4).

While the exemplary embodiments have been described in detail for clarity of understanding and by way of example, a variety of modifications, changes, and adaptations will be obvious to those who are skilled in the art. Hence, the scope of the invention is limited solely by the appended claims.

What is claimed is:

1. An eye treatment system comprising:
an eye treatment probe;
a console having:
    a console support structure,
    a plurality of cassette receptacle surfaces defining a cassette receptacle, and
    an axial translation linkage coupling the cassette receptacle to the support structure so that at least some of the cassette receptacle surfaces translate linearly along a first axis; and
a cassette configured to couple the console with the probe, the cassette having a plurality of positioning surfaces oriented for engagement by the cassette receptacle surfaces;
wherein an actuator coupled with the axial translation linkage is configured to draw the cassette toward the console such that at least some of the cassette positioning surfaces are configured to move linearly along a second axis that is disposed at an angle relative to the first axis.

2. The eye treatment system of claim 1, wherein engagement between the positioning surfaces of the cassette and the receptacle surfaces of the console inhibits rotation of the cassette as the cassette translates with the cassette receptacle.

3. The eye treatment system of claim 1, wherein the angle is about 20 degrees.

4. The eye treatment system of claim 1, wherein the angle is between 10 degrees and 30 degrees.

5. The eye treatment system of claim 1, wherein the axial translation linkage includes a first linkage portion configured for moving some of the receptacle surfaces along the first axis without rotating the receptacle surfaces, and a second linkage portion configured for moving other receptacle surfaces along a third axis without rotating the receptacle surfaces, the third axis at an angle to the first and second axes so that the receptacle surfaces more tightly constrain the positioning surfaces as the cassette moves with the cassette receptacle.

6. The eye treatment system of claim 1, wherein the cassette receptacle fittingly receives the cassette so that receptacle surfaces engage positioning surfaces and move the cassette away from the console when the linkage translates in response to an ejection command.

7. The eye treatment system of claim 1, wherein:
the console has a plurality of console surgical fluid network interfaces supported by the console support structure;
the cassette includes:
    a cassette body having a thickness along the second axis, a height, and a width, the cassette body having the positioning surfaces, and
    a plurality of cassette interfaces distributed across the height and width of the cassette body; and
translation of the axial linkage from a first location to a second location effects axial translation of each of the plurality of cassette interfaces along the second axis into engagement with a corresponding console interface.

8. The eye treatment system of claim 7, wherein the console interfaces and cassette interfaces each include at least two of:
an irrigation fluid valve interface;
an aspiration pump selection valve interface
an aspiration fluid drive interface;
an aspiration fluid pressure sensor interface;
an aspiration fluid reservoir drain drive interface;
a vent valve interface;
an aspiration fluid reservoir vacuum conduit interface; or
an aspiration fluid reservoir drain indicator interface.

9. The eye treatment system of claim 1, wherein the actuator effects translation of the cassette receptacle from a first position to a second position in response to a signal, the cassette coupling the probe to the console when the cassette is in the second position.

10. The eye treatment system of claim 9, wherein the cassette engages the console with an engagement force of over 15 pounds when the cassette is mounted to the console in the second position.

11. The eye treatment system of claim 9, wherein the cassette receptacle surfaces include first and second receptacle surfaces, wherein the first and second receptacle surfaces engage the positioning surfaces of the cassette so as to laterally constrain the cassette relative to the axis when the cassette is in the second position, movement of the axial linkage altering a lateral separation between the first and second receptacle surfaces so that the first and second receptacle surfaces accommodate a significant range of lateral misalignment of the cassette relative to the console when the cassette is in the first position.

12. The eye treatment system of claim 9, wherein the receptacle is coupled to a processor, the processor imposing a delay between engagement of the cassette against the receptacle and energizing of the actuator so as to drive the cassette to the second position.

13. The eye treatment system of claim 9, wherein the cassette receptacle comprises a plurality of channels that receive and slide over associated flanges of the cassette, and wherein the axial linkage comprises a plurality of shafts that slide in an associated plurality of guides, the shafts being angled relative to the axis so as to move the channels over the flanges during mounting of the cassette, the shafts being coupled to the actuator by a cam and roller.

* * * * *